(12) United States Patent
Taweh

(10) Patent No.: US 12,109,343 B2
(45) Date of Patent: Oct. 8, 2024

(54) DIALYSIS TREATMENT FACILITY WALL-BOX APPARATUS

(71) Applicant: George Taweh, Farmington, CT (US)

(72) Inventor: George Taweh, Farmington, CT (US)

(73) Assignee: George Tawch, Farmington, CT (US)

( * ) Notice: Subject to any disclaimer, the term of this patent is extended or adjusted under 35 U.S.C. 154(b) by 304 days.

(21) Appl. No.: 17/655,546

(22) Filed: Mar. 19, 2022

(65) Prior Publication Data

US 2023/0293789 A1 Sep. 21, 2023

(51) Int. Cl.
*A61M 1/16* (2006.01)

(52) U.S. Cl.
CPC ....... *A61M 1/1657* (2022.05); *A61M 2209/08* (2013.01)

(58) Field of Classification Search
CPC ... A61M 1/1656; A61M 1/1657; E03C 1/021; Y10T 137/698
See application file for complete search history.

(56) References Cited

U.S. PATENT DOCUMENTS

| | | | | |
|---|---|---|---|---|
| 3,774,762 | A * | 11/1973 | Lichtenstein | A61M 1/1561 210/321.71 |
| 4,498,693 | A * | 2/1985 | Schindele | A61G 13/107 248/223.41 |
| 5,197,511 | A * | 3/1993 | Kohn | F16L 37/60 251/149.6 |
| 5,282,488 | A | 2/1994 | Roth | |
| 6,197,197 | B1 * | 3/2001 | Peterson | H02G 3/0487 210/252 |
| 7,174,678 | B2 * | 2/2007 | Gallant | A61G 12/00 52/64 |
| 8,496,029 | B2 | 7/2013 | Vu | |
| 9,421,312 | B1 | 8/2016 | Marinan et al. | |
| D995,785 | S * | 8/2023 | Taweh | D24/169 |
| 2002/0000402 | A1 * | 1/2002 | Dillon | A61M 1/16 210/232 |
| 2008/0015493 | A1 * | 1/2008 | Childers | A61M 1/167 604/29 |
| 2009/0145493 | A1 * | 6/2009 | Lee | E03C 1/021 137/360 |
| 2010/0051529 | A1 * | 3/2010 | Grant | A61M 60/113 210/232 |
| 2010/0095604 | A1 * | 4/2010 | Newkirk | E04F 19/08 52/220.7 |

(Continued)

*Primary Examiner* — Reinaldo Sanchez-Medina
*Assistant Examiner* — Nicole Gardner
(74) *Attorney, Agent, or Firm* — EMANUS LLC; Willie Jacques

(57) ABSTRACT

A dialysis treatment facility wall-box apparatus is disclosed. The dialysis treatment facility wall-box comprises a main body having a first portion and a second portion. Further, the dialysis treatment facility wall-box apparatus comprises a tether line connected to the first portion of the main body of the dialysis treatment facility wall-box apparatus via an anchor fitting. The anchor fitting is tightened through the dialysis treatment facility wall-box apparatus. A plurality of fly loop lines is positioned at inner portion and outer portion of the wall-box. A tea fitting is coupled to the anchor fitting through the plurality of fly loop lines at the inner portion. Further, the dialysis treatment facility wall-box apparatus comprises a first plurality of loops and a second plurality of loops.

20 Claims, 14 Drawing Sheets

(56) References Cited

U.S. PATENT DOCUMENTS

| | | | |
|---|---|---|---|
| 2010/0140149 A1 | 6/2010 | Fulkerson | |
| 2011/0041928 A1* | 2/2011 | Volker | A61M 1/1668 |
| | | | 137/240 |
| 2011/0219706 A1* | 9/2011 | Bates | A47B 97/001 |
| | | | 52/27 |
| 2011/0315237 A1* | 12/2011 | Jenkins | A61M 1/16 |
| | | | 137/312 |
| 2012/0031502 A1* | 2/2012 | Randall | A61M 1/1682 |
| | | | 137/15.01 |
| 2015/0314056 A1 | 11/2015 | Giordano et al. | |
| 2019/0186110 A1* | 6/2019 | Taweh | A61M 39/105 |
| 2020/0268957 A1* | 8/2020 | Schmitt | A61M 1/1668 |
| 2022/0040390 A1* | 2/2022 | Robertson | A61M 1/1609 |

* cited by examiner

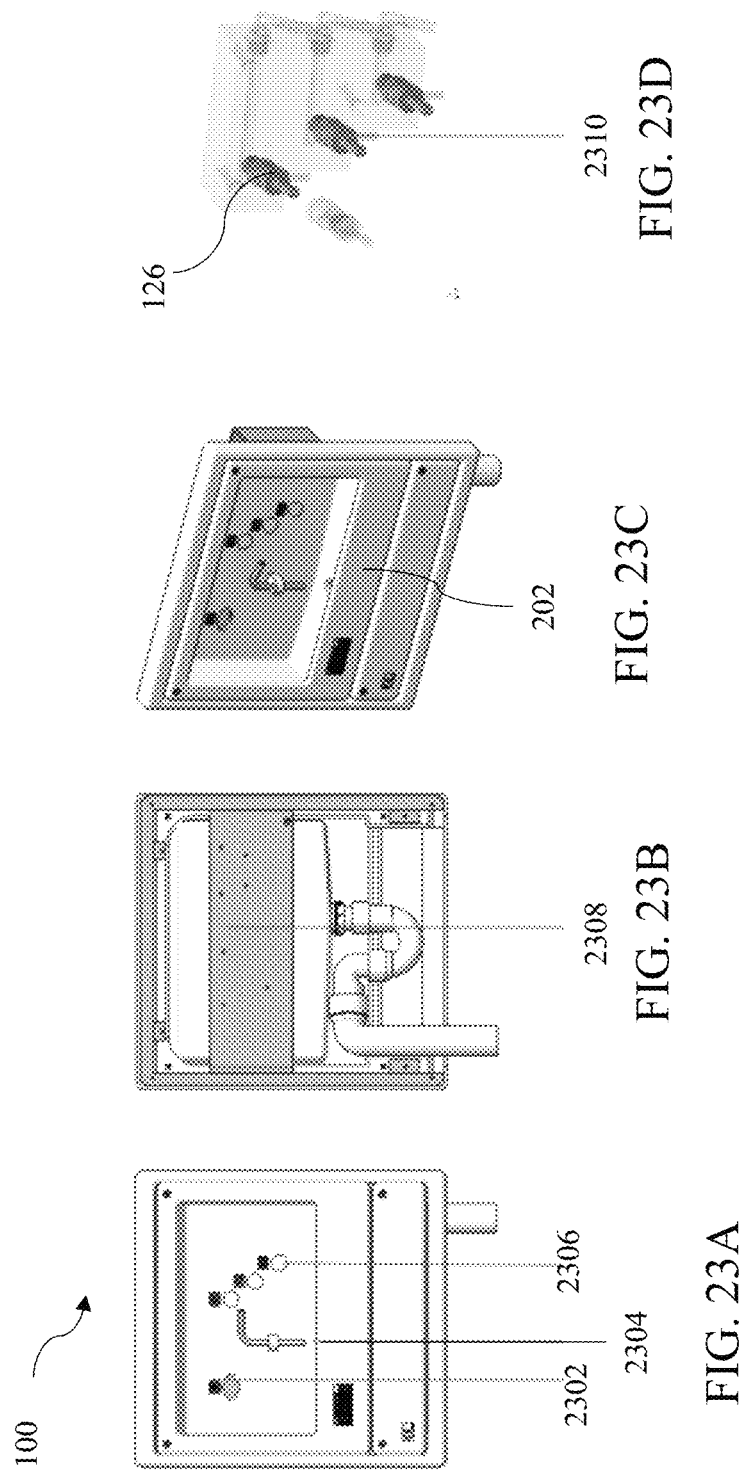

DIALYSIS TREATMENT FACILITY WALL-BOX APPARATUS

FIELD OF THE DISCLOSURE

The invention generally relates to a wall-box apparatus for routing plumbing lines within an interior of a building structure and connecting to machines within the building structure. More particularly, the invention relates to a dialysis treatment facility wall-box apparatus for a medical treatment facility.

BACKGROUND OF THE DISCLOSURE

The subject matter discussed in this background section should not be assumed to be prior art merely as a result of its mention herein. Similarly, any problems mentioned in this background section or associated with the subject matter of this background section should not be assumed to have been previously recognized in the prior art. The subject matter as disclosed in this background section merely represents different approaches related to a dialysis treatment facility wall-box apparatus, wherein such dialysis treatment facility wall-box apparatus themselves may also correspond to implementations of the claimed technology and invention.

Dialysis is a specialty treatment in medical science for the treatment of acute and chronic kidney failure, which can lead to death if untreated for several days or weeks. Medical science has been advancing for the past few decades by employing sophisticated medical devices with advanced mechanical components. The advancement in dialysis machines, is happening at a rapid rate over the past few years. The dialysis acts as an artificial kidney by filtering toxins, waste, and fluid from the blood through a semipermeable membrane. The semipermeable membrane is a film that allows fluids and fine particles to flow through it. Typically, the dialysis includes two types, such as, a hemodialysis and a peritoneal dialysis, which use different methods to filter toxins from the body.

The hemodialysis is performed using, a filtering membrane which is called a dialyzer and is present inside the dialysis machine. In this case, patient's blood is circulated through the dialysis machine and cleaned before being returned to the patient's body. The peritoneal dialysis is performed using, the filtering membrane as the natural lining of patient's peritoneum or abdomen and blood never leaves the patient's body. The hemodialysis and the peritoneal dialysis also use a dialysate solution in the filtering process to help remove unwanted substances. In order to perform both the hemodialysis and the peritoneal dialysis, a dialysis system is set up facilitating both types of the dialysis process. However, the challenge in the dialysis system to perform both the hemodialysis and the peritoneal dialysis is that there is inconvenience and increase in cost in interior design, maintenance, operation, and installation of the dialysis system.

To perform the dialysis efficiently, a dialysis service box was introduced. Dialysis service boxes are frames recessed into a wall at each hemodialysis station that contain connections for a dialysis machine to receive acid and base concentrates, to treat water, and dispose of waste products. The dialysis service box is used as a station box to help connect central distribution systems to a hemodialysis machine. Every dialysis service box serves as a workstation for each patient treatment area, conveniently accepting connections for reverse osmosis (RO) or Deionized (DI), bicarbonate and acid concentrate. The current dialysis service box provides water treatment solutions and dialysis treatment by incorporating all units and components of the dialysis treatment facility wall-box outside and thereby utilizing more dead space for piping and arrangements. Further, the current dialysis service box employs the dialysis treatment facility wall-box for a single patient at a time.

Prior art, for various aspects contained there within, relevant to this disclosure includes U.S. Pat. Publication No 2012/0031502 to Jeff Randall, U.S. Pat. No. 9,421,312 to Kevin and U.S. Pat. No. 9,526,820 to Michael James Beiriger. In all of these prior art references, a wall-box system is designed for a plumbing arrangement of the dialysis machine. The art still begs for an ideal solution to the problem of the inability to manage the flow of RO water through the wall-box and preventing RO water to sit in areas making conditions for bacterial growth more likely to occur.

In particular, reference '502 to Randall discloses the dialysis service box which includes a plumbing arrangement having a supply inlet for supplying a fluid to a dialysis machine, a backflow preventer for preventing retrograde flow through the plumbing arrangement, a trap primer for maintaining a trap seal designed to prevent waste gases from flowing into the dialysis service box and a waste connection for allowing waste from the dialysis machine to exit. The dialysis service box can be universally installed to operate, control, and adjust any dialysis machine that requires supply connection, waste connection, backflow preventer, and trap primer, or any combination. However, unlike the subject matter of the disclosed invention, Randall does not discuss or suggest the management of the flow of fluid through the dialysis service box. Further, Randall does not suggest or disclose prevention of the fluid from sitting in areas, thereby making conditions for bacterial growth less likely to occur.

Reference '312 to Kevin discloses a modular wall-chase system relating to the routing of mechanical elements (plumbing, electrical, data, etc.) within the interior of a new, or already built, structure and particularly relating to the interior of a kidney-dialysis treatment facility. The modular wall-chase system comprises a fluid collector which includes an opening to access an interior cavity, a horizontally oriented basin partially bounding the interior cavity, and a fluid drain line connected to the basin. However, unlike the subject matter of the disclosed invention, Kevin does not discuss or suggest the aspect of creating a continuous flow of fluid to a connection at an interior of kidney-dialysis treatment facility. Kevin also does not suggest or disclose prevention of the fluid from sitting in areas, thereby making conditions for bacterial growth less likely to occur.

Reference '820 to James discloses a dialysis system that includes a housing, a dialysate pump disposed in the housing, and a dialysate line configured to be operatively connected to the dialysate pump such that the dialysate pump can pump dialysate through the dialysate line when the dialysate line is in fluid communication with a dialysate source. However, unlike the subject matter of the disclosed invention, James does not discuss or suggest the aspect of management of the flow of fluid through the dialysis system. James also does not suggest or disclose prevention of the fluid from sitting in areas, thereby making conditions for bacterial growth less likely to occur.

The current market solutions for the management of the flow of fluid through plumbing lines to the interior of the building, especially dialysis systems, all involve a dialysis service box having a fluid collector which includes an opening to access the interior of the building. Therefore, in light of the above discussion and given the deficiencies of the current dialysis boxes, there is a need for a dialysis wall-box to manage the flow of fluid through the wall-box and to prevent the fluid from sitting in areas or sticking to the areas, thereby making conditions for bacterial growth less likely to occur.

SUMMARY OF THE DISCLOSURE

According to embodiments illustrated herein, a novel, simple, and easy-to-use dialysis treatment facility wall-box apparatus is disclosed. The dialysis treatment facility wall-box apparatus comprises a main body having a first portion and a second portion spaced apart from the first portion and enclosed in a wall-box housing. The first portion and the second portion of the main body are integrated with a plurality of fluid lines and valves to facilitate the flow of fluid towards a dialysis machine. Further, the dialysis treatment facility wall-box apparatus comprises a tether line connected to the first portion of the main body using an anchor fitting. The anchor fitting is integrated into the first portion of the main body. The anchor fitting is a hook affixed to the first portion of the main body. Further, the dialysis treatment facility wall-box apparatus comprises a tee-fitting positioned in a space between the first portion and the second portion of the main body. The tee-fitting is coupled to the anchor fitting through a plurality of fly loop lines protruding towards the first portion of the main body. Further, the dialysis treatment facility wall-box apparatus comprises a first plurality of loops positioned at a first end of the main body and a second plurality of loops positioned at a second end of the main body. The first plurality of loops and the second plurality of loops extended normally outwards of the main body. Further, the dialysis treatment facility wall-box apparatus comprises a fly loop combo line coupled to the first portion of the wall-box housing at a first end of the fly loop combo line and connected to a dialysis machine at a second end of the fly loop combo line. The fly loop combo line is connected to the tether line which is attached to the anchor fitting, to hold the fly loop combo line attached to the main body. The fly loop combo line creates a continuous flow of fluid downwards to the dialysis machine, and then flows back to the tee-fitting and into the first plurality of loops. Such use of the dialysis treatment facility wall-box apparatus facilitates reducing the number of joints in plumbing systems and thus increasing available space in a building. Further, the dialysis treatment facility wall-box apparatus eliminates a requirement of shelves and cabinets to increase space for the dialysis treatment facility.

Further, the dialysis treatment facility wall-box apparatus comprises a fluid inlet attached at a first end of the tee-fitting, and a fluid outlet attached at a second end of the tee-fitting. The fluid inlet and the fluid outlet are coupled to the tee-fitting horizontally within the space between the first portion and the second portion of the main body. Further, the dialysis treatment facility wall-box apparatus comprises a plurality of valves coupled to the first portion of the main body. It can be noted that each of the plurality of valves is detachable from the wall-box. Further, the dialysis treatment facility wall-box apparatus comprises a plurality of flow control valves integrated over a surface of the first portion and protruding normal to the surface of the first portion. In one embodiment, each of the plurality of flow control valves is configured to facilitate a movement of fluid towards each of the plurality of valves. In one embodiment, the plurality of flow control valves is coupled with a plurality of valve regulators to regulate the flow of the fluid towards the plurality of valves. In one embodiment, the wall-box housing is constructed from a material, selected from a group of materials of, rubber, wood, polyethylene (PE), high-density polymer (HDPE).

In one embodiment, the first plurality of loops and the second plurality of loops are tightened to the first portion of the main body using a first plurality of screws. The first plurality of loops and the second plurality of loops are coupled on either side of the first portion of the main body. The first portion of the main body comprises a plurality of opening of the first plurality of loops and a plurality of opening of the second plurality of loops. The plurality of openings of the first plurality of loops and the second plurality of loops are integrated on either side of the first portion of the main body.

In one embodiment, the wall-box housing is coupled to the main body using a second plurality of screws and the wall-box housing encloses, the main body coupled with the first plurality of loops, the second plurality of loops, the plurality of flow control valves, the tee-fitting, the anchor fitting, and the tether line. In one embodiment, the dialysis treatment facility wall-box apparatus comprises a plurality of fluid flow conduits configured to accommodate fluid flow control and communication between a plurality of fluid sources in the dialysis treatment facility. Further, the dialysis treatment facility wall-box apparatus comprises a plurality of connecting ports configured to receive the plurality of loop lines and the plurality of plumbing lines. In one embodiment, the plurality of fluid conduits is made from a material or a combination of materials selected from a group of materials of fiber, rubber, PE, HDPE, polyvinylchloride (PVC), alloy steel, and stainless steel.

In one embodiment, the dialysis treatment facility wall-box apparatus is configured to reduce the number of joints in plumbing systems. In another embodiment, the dialysis treatment facility wall-box apparatus is configured to increase available space in a building. The dialysis treatment facility wall-box apparatus eliminates a requirement of shelves and cabinets to increase space for the dialysis treatment facility. Further, the dialysis treatment facility wall-box apparatus comprises a bumper clip to provide an organized manner for snapping fluid lines and to serve as a fastening means for a P-shaped bumper railing to snap onto the fluid lines. The fluid lines include one RO fluid line and one bicarb line and two acid lines.

In one embodiment, the dialysis treatment facility wall-box apparatus comprises reverse osmosis (RO) water inlet attached at one end of the tee-fitting and an RO water outlet attached at a second end of the tee-fitting. It can be noted that the RO water inlet and the RO water outlet correspond to the fluid inlet and the fluid outlet. In one embodiment, the fluid may include, but not limited to, dialysate, pure water, electrolytes, salts, bicarbonate, and sodium.

In another embodiment, a method for managing the flow of fluid through the dialysis treatment facility wall-box apparatus is disclosed. The method comprises providing a main body with a first portion and a second portion spaced apart from the first portion and enclosed in a wall-box housing. The method further comprises providing a tether line connected to the first portion of the main body of the wall-box via an anchor fitting integrated to the first portion of the main body. Further, the method comprises providing a plurality of fly loop lines protruding towards the first portion of the main body of the wall-box. The method further comprises connecting a tee-fitting in a space between the first portion and the second portion of the main body. The tee-fitting is coupled to the anchor fitting through a plurality of fly loop lines protruding towards the first portion of the main body. Further, the method comprises positioning a first plurality of loops at a first end of the main body and a second plurality of loops at a second end of the main body. The first plurality of loops and the second plurality of loops extended normally outwards of the wall-box. The method further comprises connecting a fly loop combo line, coupled to the first portion of the wall-box housing, at a first end of the fly loop combo line, to a dialysis machine, at a second end of the fly loop combo line, to create a continuous flow of fluid downwards to a connection at the dialysis machine, then flows back to the tee-fitting and into the first plurality of loops. Such a method of managing fluid flow through a dialysis treatment facility wall-box apparatus facilitates reducing the number of joints in plumbing systems and thus increasing available space in a building. Further, the dialysis treatment facility wall-box apparatus eliminates a requirement of shelves and cabinets to increase space for the dialysis treatment facility.

Further, the method comprises providing a fluid inlet attached at a first end of the tee-fitting, and a fluid outlet attached at a second end of the tee-fitting. The fluid inlet and the fluid outlet are coupled to the tee-fitting horizontally within the space between the first portion and the second portion of the main body. Further, the method comprises providing a plurality of valves coupled to the first portion of the main body. It can be noted that each of the plurality of valves is detachable from the wall-box. Further, the method comprises providing a plurality of flow control valves integrated over a surface of the first portion and protruding normal to the surface of the first portion. In one embodiment, each of the plurality of flow control valves is configured to facilitate a movement of fluid towards each of the plurality of valves.

Further, the first plurality of loops and the second plurality of loops are tightened to the first portion of the main body using a first plurality of screws. The first plurality of loops and the second plurality of loops are coupled on either side of the first portion of the main body. The first portion of the main body comprises a plurality of opening of the first plurality of loops and a plurality of opening of the second plurality of loops. The plurality of openings of the first plurality of loops and the second plurality of loops are integrated on either side of the first portion of the main body.

In one embodiment, the wall-box housing is coupled to the main body using a second plurality of screws and the wall-box housing encloses, the main body coupled with the first plurality of loops, the second plurality of loops, the plurality of flow control valves, the tee-fitting, the anchor fitting, and the tether line. In one embodiment, the plurality of flow control valves is coupled with a plurality of valve regulators to regulate the flow of the fluid towards the plurality of valves. In one embodiment, the wall-box housing is constructed from a material, selected from a group of materials of, rubber, wood, polyethylene (PE), high-density polymer (HDPE).

In one embodiment, the method comprises facilitating fluid flow control and communication using a plurality of fluid flow conduits, between a plurality of fluid sources in the dialysis treatment facility. Further, the method comprises receiving the plurality of loop lines and the plurality of plumbing lines into a plurality of connecting ports. In one embodiment, the plurality of fluid conduits is made from a material or a combination of materials selected from a group of materials of fiber, rubber, PE, HDPE, polyvinylchloride (PVC), alloy steel, and stainless steel.

In one embodiment, the method is configured to reduce the number of joints in plumbing systems. In another embodiment, the method is configured to increase available space in a building. The method eliminates the requirement of shelves and cabinets to increase space for the dialysis treatment facility. Further, the method comprises providing a bumper clip to provide an organized manner for snapping fluid lines and to serve as a fastening means for a P-shaped bumper railing to snap onto the fluid lines. The fluid lines include one RO fluid line, one bicarb line, and two acid lines. Other features and aspects of this disclosure will be apparent from the following description and the accompanying drawings.

BRIEF DESCRIPTION OF THE DRAWINGS

While the specification concludes with claims particularly pointing out and distinctly claiming particular embodiments of the present disclosure, various embodiments of the present disclosure can be more readily understood and appreciated from the following descriptions of various embodiments of the present disclosure when read in conjunction with the accompanying drawings, in which:

FIGS. 23A-23D illustrate a wall-box apparatus mounted inside the wall of the dialysis facility room, according to another embodiment of the present disclosure.

DETAILED DESCRIPTION

Reference will now be made in detail to specific embodiments or features, examples of which are illustrated in the accompanying drawings. Wherever possible, corresponding or similar reference numbers will be used throughout the drawings to refer to the same or corresponding parts. Moreover, references to various elements described herein, are made collectively or individually when there may be more than one element of the same type. However, such references are merely exemplary in nature. It may be noted that any reference to elements in the singular may also be construed to relate to the plural and vice-versa without limiting the scope of the disclosure to the exact number or type of such elements unless set forth explicitly in the appended claims.

Some embodiments of this disclosure, illustrating all its features, will now be discussed in detail. The words "comprising," "having," "containing," and "including," and other forms thereof, are intended to be equivalent in meaning and be open-ended in that an item or items following any one of these words is not meant to be an exhaustive listing of such item or items, or meant to be limited to only the listed item or items.

It must also be noted that as used herein and in the appended claims, the singular forms "a," "an," and "the" include plural references unless the context dictates otherwise. Although any systems and methods similar or equivalent to those described herein can be used in the practice or testing of embodiments of the present disclosure, the preferred systems, and methods are now described.

Embodiments of the present disclosure will be described more fully hereinafter with reference to the accompanying drawings in which like numerals represent like elements throughout the several figures, and in which example embodiments are shown. Embodiments of the present disclosure may, however, be embodied in alternative forms and should not be construed as being limited to the embodiments set forth herein. The examples set forth herein are non-limiting examples and are merely examples among other possible examples.

Figure 1:
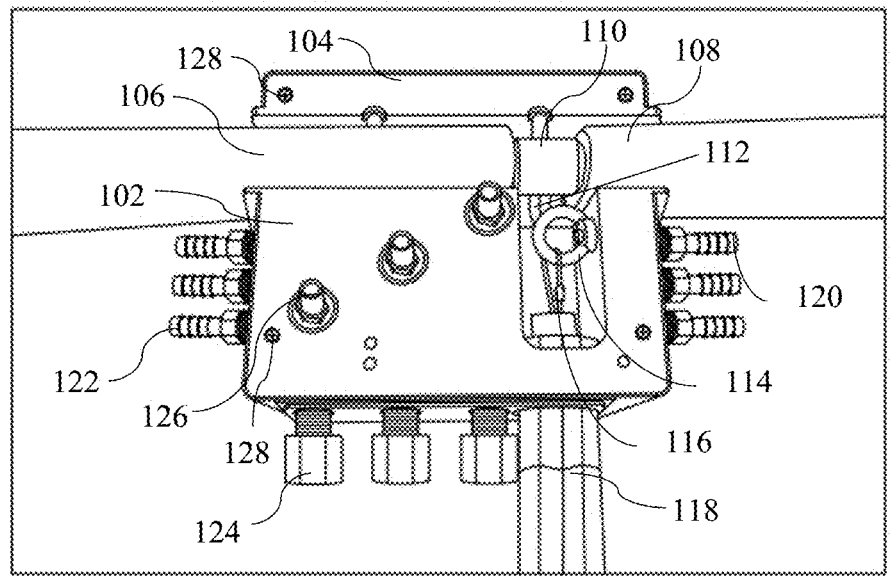
FIG. 1 illustrates a front perspective view of a dialysis treatment facility wall-box apparatus, according to an embodiment of the present disclosure.

FIG. 1 illustrates a front perspective view of a dialysis treatment facility wall-box apparatus 100, according to an embodiment. The dialysis treatment facility wall-box apparatus 100 may be of a cubical or box-shaped facility wall-mounted box. In one embodiment, the dialysis treatment facility wall-box apparatus 100 may be a fluid transport housing employed in dialysis treatment and other healthcare treatments. In one embodiment, the dialysis treatment facility wall-box apparatus 100 is constructed from a material selected from a group of materials of polyvinyl chloride (PVC), cross-linked polyethylene (PEX) material, and has overall dimensions of approximately 7.0"×3.0"×5.0". In one embodiment, the dialysis treatment facility wall-box apparatus 100 may have size and shape according to the requirement of a medical facility, such as cylindrical, hexagonal, etc. Hereinafter, the dialysis treatment facility wall-box apparatus 100 may be referred to as a wall-box apparatus 100. In one embodiment, the wall-box apparatus 100 may be assembled using different mechanical processes such as machining, molding, sonic welding, thermal press, or other suitable construction means. It can be noted that the wall-box 100 may be configured to increase available space in a building. Further, the wall-box apparatus 100 may be constructed to withhold fluid flow pressure. In one embodiment, the wall-box apparatus 100 may be sized such that fluid lines have minimum wall thickness to withhold an internal pressure of the fluids being transported. It can be noted that the overall dimensions of the wall-box apparatus 100 are constrained, only by the thinnest wall thickness.

In one exemplary embodiment, the wall-box apparatus 100 may be employed for the management of the flow of water through the wall-box apparatus 100. The wall-box apparatus 100 may prevent the spread of infection within fluid lines in the wall-box apparatus 100. The wall-box apparatus 100 may comprise a main body having a first portion 102 and a second portion 104. The first portion 102 and the second portion 104 may be configured to hold a plurality of components of the wall-box apparatus 100 in an ordered fashion to make fluid flow smooth. Further, the wall-box apparatus 100 may comprise a fluid inlet 106 and a fluid outlet 108 connected to the main body. The main body comprises a tee-fitting 110, having a first end and a second end, disposed between the first portion 102 and the second portion 104 and connected at the first end to the fluid inlet 106 and at the second end to the fluid outlet 108. In one embodiment, the fluid inlet 106 and the fluid outlet 108 may be referred to as an inlet fluid conduit and an outlet fluid conduit coupled to the tee-fitting 110 between the first portion 102 and the second portion 104. In one embodiment, the fluid inlet 106 and the fluid outlet 108 may be reverse osmosis (RO) water inlet and outlet. The wall-box apparatus 100 may further comprise a plurality of fly loop lines 112, an anchor fitting 114, a tether line 116, and a fly loop combo line 118.

The tether line 116 may be connected to the first portion 102 of the main body using the anchor fitting 114. The anchor fitting 114 may be integrated into the first portion 102 of the wall-box apparatus 100. The tee-fitting 110 may be positioned in a space between the first portion 102 and the second portion 104 of the main body of the wall-box apparatus 100. The tee-fitting 110 may be coupled to the anchor fitting 114 through the plurality of fly loop lines 112 protruding towards the first portion 102 of the main body. The fly loop combo line 118 may comprise a first end and a second end. The fly loop combo line 118 may be coupled to the first portion 102 of the wall-box apparatus 100 at the first end and to a dialysis machine (not shown) at the second end. It can be noted that the fly loop combo line 118 creates a continuous flow of fluid downwards to a connection at the dialysis machine and then flows back to the tee-fitting 110. Further, the wall-box apparatus 100 may comprise a first plurality of loops 120 positioned at a first end of the main body and a second plurality of loops 122 positioned at a second end of the main body. The first plurality of loops 120 and the second plurality of loops 122 extended normally outwards of the main body. In one embodiment, the fly loop combo line 118 creates the continuous flow of the fluid downwards to the connection at the dialysis machine and then flows back to the tee-fitting 110 and into the first plurality of loops 120.

Further, the wall-box apparatus 100 may comprise a plurality of valves 124 may be positioned at a bottom side of the first portion 102 of the main body. In one embodiment, each of the plurality of valves 124 may be detachable from the wall-box apparatus 100. Further, the wall-box apparatus 100 may comprise a plurality of flow control valves 126 positioned at the first portion 102 of the main body. Further, the plurality of flow control valves 126 integrated over a surface of the first portion 102 and protruding normal to the surface of the first portion 102. In one embodiment, each of the plurality of flow control valves 126 may be configured to facilitate a movement of fluid towards each of the plurality of valves 124. Further, the wall-box apparatus 100 may comprise a first plurality of screws 128 configured to couple the first plurality of loops 120 and the second plurality of loops 122 to the first portion 102 of the main body. In one embodiment, each of the first plurality of screws 128 of the wall-box apparatus 100 is positioned at the first portion 102 of the main body to provide a tightening arrangement between the first plurality of loops 120 and the wall-box apparatus 100.

Figure 2:
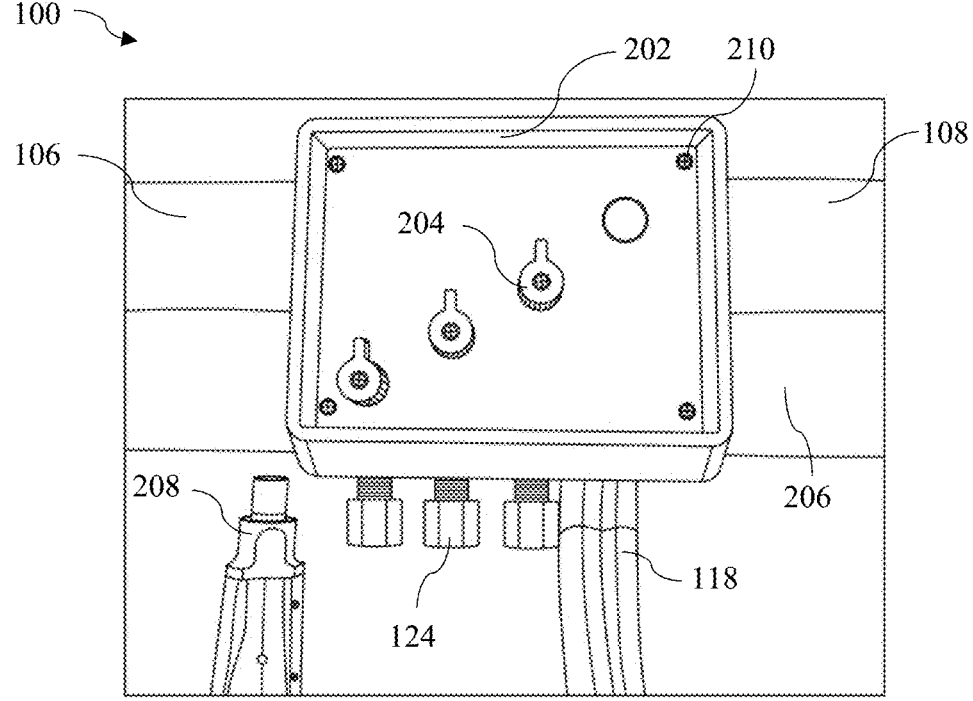
FIG. 2 illustrates an enclosed view of the dialysis treatment facility wall-box apparatus, according to an embodiment of the present disclosure.
Figure 8:
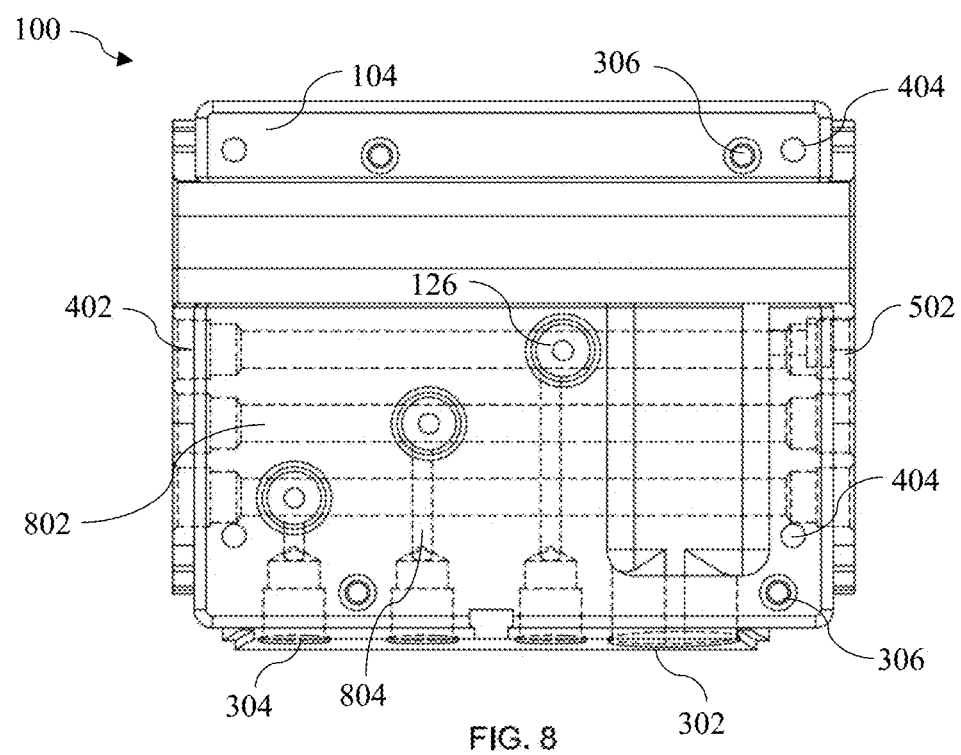
FIG. 8 illustrates a front view of the dialysis treatment facility wall-box apparatus integrated within loops and valves, according to another embodiment of the present disclosure.

FIG. 2 illustrates an enclosed view of the dialysis treatment facility wall-box apparatus 100. The wall-box apparatus 100 may comprise a wall-box housing 202, a plurality of valve regulators 204, a housing 206 of the first plurality of loops 120, and the second plurality of loops 122, another fly loop combo line 208, and a second plurality of screws 210. In one exemplary embodiment, the wall-box housing 202 may be a solid block covering the first portion 102, the second portion 104, the tee-fitting 110 from inside of the wall-box apparatus 100. Further, the wall-box apparatus 100 may comprise the plurality of valve regulators 204 positioned on the wall-box housing 202. The plurality of valve regulators 204 may be coupled to the plurality of flow control valves 126. In one embodiment, the plurality of valve regulators 204 may regulate the flow of fluids into their respective fluid flow conduits (as shown in FIG. 8) that routes fluid flow to respective plumbing lines. It can be noted that the number of the first plurality of loops 120 and the second plurality of loops 122 coupled to the first portion 102 of the main body of the wall-box apparatus 100 and interconnecting with respective fluid flow conduits, depends upon the number and types of fluids to be delivered to a hemodialysis station.

The housing 206 of the first plurality of loops 120 and the second plurality of loops 122 may be connected adjacent to the wall-box housing 202. Further, the housing 206 of the first plurality of loops 120 and the second plurality of loops 122 surrounds the wall-box housing 202 and other mechanical components of the wall-box apparatus 100. The housing 206 of the first plurality of loops 120 and the second plurality of loops 122 may provide mechanical support to the moving components such as the plurality of valve regulators 204. Further, the wall-box apparatus 100 may comprise another fly loop combo line 208 mounted on a bottom portion of the wall-box apparatus 100 and positioned adjacent to the plurality of valves 124 and the fly loop combo line 118. It can be noted that the another fly loop combo line 208 is provided in case of the fly loop combo line 118 may get clogged or any damage may occur during dialysis treatment. It can also be noted that the another fly loop combo line 208 is provided to supply the fluid to multiple dialysis machines from a single dialysis treatment facility wall-box apparatus 100. Further, the wall-box apparatus 100 may comprise the second plurality of screws 210 positioned at the first portion 102 of the main body to provide a tightening arrangement between the second plurality of loops 122 and the wall-box apparatus 100. In one embodiment, the second plurality of screws 210 may be attached with the first portion 102 of the main body through linkages, joints, or retention members.

In one embodiment, the wall-box apparatus 100 may eliminate the need for shelving and cabinetry in the dialysis treatment facilities and thereby increase space in the dialysis treatment facility. Further, the wall-box apparatus 100 may provide concurrent fluid flow communication to a plurality of dialysis machines on opposite sides of the dialysis treatment facility wall-box apparatus 100. In another embodiment, the wall-box apparatus 100 may provide a clip to snap in fluid lines up to a single fluid line and three bicarb and acid lines. Further, the wall-box apparatus 100 may be configured to improve safety, reducing leaks, and reducing infection stemming during the dialysis treatment.

Figure 3:
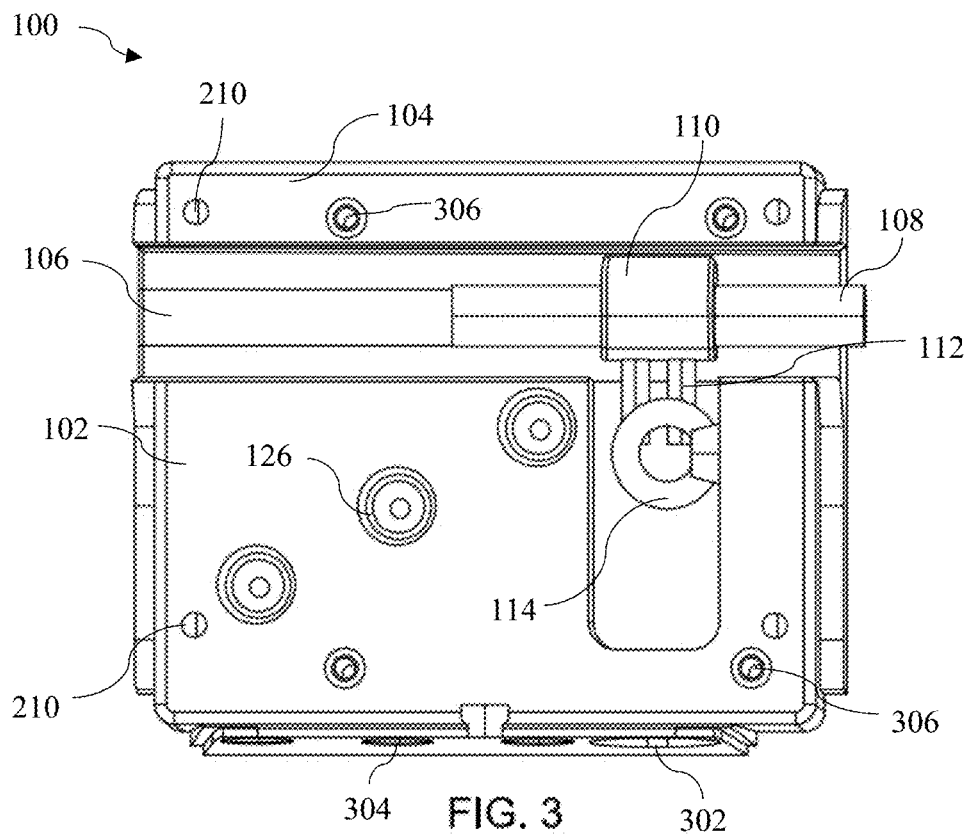
FIG. 3 illustrates a front view of the dialysis treatment facility wall-box apparatus with a first tee-fitting lines coupled behind a tether line, according to an embodiment of the present disclosure.

FIG. 3 illustrates a front view of the dialysis treatment facility wall-box apparatus 100 with the plurality of fly loop lines 112 coupled behind the tether line 116, according to an embodiment. The wall-box apparatus 100 may comprise a first outlet opening 302 for the fly loop combo line 118 positioned towards a bottom side of the first portion 102 of the wall-box apparatus 100. It can be noted that the first outlet opening 302 for the fly loop combo line 118 is a section of the first portion 102 through which the fly loop combo line 118 provides a passage for continuous flow of the fluid to the connection at the dialysis machine. Further, the wall-box apparatus 100 may comprise a second outlet opening 304 for the plurality of valves 124. In one embodiment, the plurality of valves 124 pushes out the flow of fluid through the second outlet opening 304, to regulate the flow of the fluid. In one embodiment, the wall-box apparatus 100 may be referred as a Bernoulli T-Box employing Bernoulli effect of fluid flowing to and from between the wall-box apparatus 100 and the dialysis treatment machine. It can be noted that the Bernoulli effect employs that a pressure decrease is associated with an increase in fluid speed, and increased pressure is associated with a decrease in fluid speed. It can also be noted that the when the fluid flows from the tee-fitting 110 towards the dialysis treatment machine, there is a decrease in pressure and increase in speed of fluid within the fly loop combo line 118, and when the fluid flows upwards from the dialysis treatment machine to the wall-box apparatus 100, there is a decrease in speed and increase in pressure of fluid.

Further, the wall-box apparatus 100 may comprise a first plurality of holes 306 integrated into the first portion 102 and the second portion 104 of the main body. In one embodiment, each of the first portion 102 and the second portion 104 may be integrated with at least two holes of the first plurality of holes 306. In an embodiment, the first plurality of holes 306 may be integrated at both sides of the fluid inlet 106 and the fluid outlet 108. The fluid inlet 106 and the fluid outlet 108 are attached at opposite ends of the tee-fitting 110. In an embodiment, each of the first plurality of holes 306 is integrated adjacent to the first plurality of screws 128 of the wall-box apparatus 100.

Figure 4:
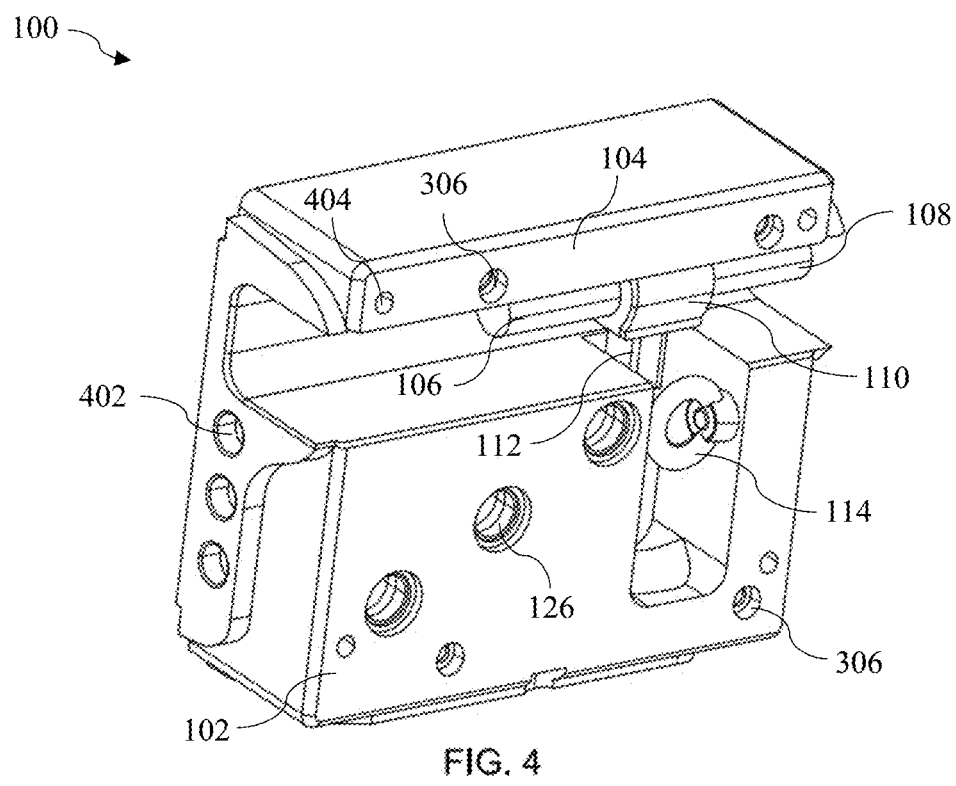
FIG. 4 illustrates another front view of the dialysis treatment facility wall-box apparatus with an inlet valve and an outlet valve, according to an embodiment of the present disclosure.

FIG. 4 illustrates a perspective view of the dialysis treatment facility wall-box apparatus 100, according to an embodiment. The wall-box apparatus 100 may comprise a plurality of outlet openings 402 of the second plurality of loops 122 integrated at the first portion of the main body. In one embodiment, the plurality of outlet openings 402 of the second plurality of loops 122 may be integrated towards one side end of the first portion 102 of the main body. The plurality of outlet openings 402 of the second plurality of loops 122 may receive fluid passing through the second plurality of loops 122 and may provide a passage for the fluid to flow through the second plurality of loops 122. Further, the wall-box apparatus 100 may comprise a second plurality of holes 404 integrated over the first portion 102 and the second portion 104 of the main body. The second plurality of holes 404 may receive the second plurality of screws 210 to attach the wall-box housing 202 onto the main body. In one embodiment, the second plurality of holes 404 may be integrated at both sides of the fluid inlet 106 and the fluid outlet 108. In an embodiment, the second plurality of holes 404 lies adjacent to the flow control valves 126 at the first portion 102.

Figure 5:
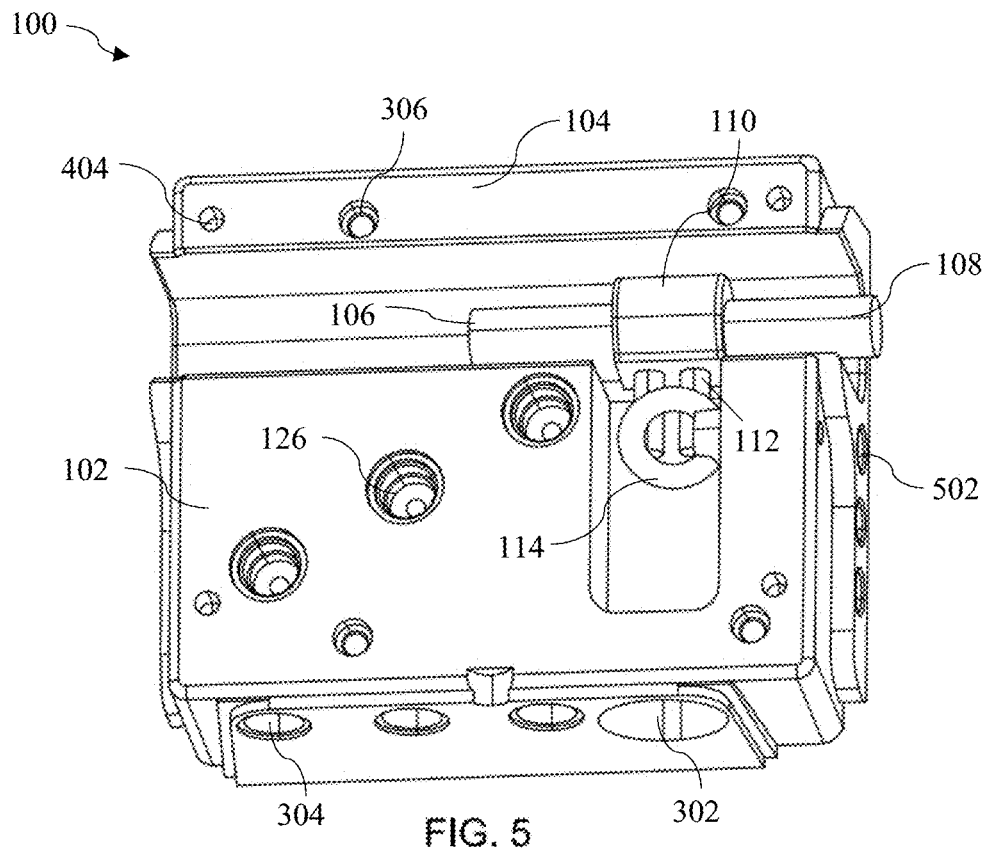
FIG. 5 illustrates another perspective view of the dialysis treatment facility wall-box apparatus with a first plurality of loops integrated on a first side, according to an embodiment of the present disclosure.
Figure 6:
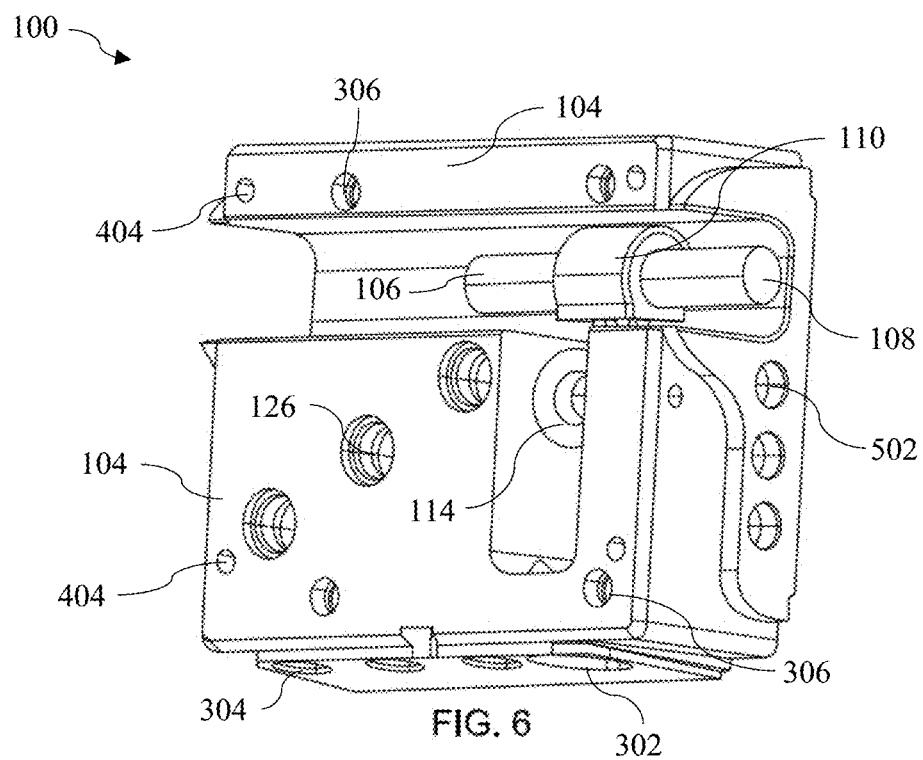
FIG. 6 illustrates another perspective view of the dialysis treatment facility wall-box apparatus with a second plurality of loops integrated on a second side, according to an embodiment of the present disclosure.

FIGS. 5-6 illustrate perspective views of the dialysis treatment facility wall-box apparatus 100, according to an embodiment. The wall-box apparatus 100 may comprise the first portion 102 of the main body, the second portion 104 of the main body, the fluid inlet 106, the fluid outlet 108, the tee-fitting 110, the plurality of fly loop lines 112, the anchor fitting 114, the plurality of flow control valves 126, the first outlet opening 302 of the fly loop combo line 118, the second outlet opening 304 of the plurality of valves 124, the first plurality of holes 306, the second plurality of holes 404. Further, the wall-box apparatus 100 may comprise a plurality of outlet openings 502 of the first plurality of loops 120. The plurality of outlet openings 502 of the first plurality of loops 120 may receive fluid passing through the first plurality of loops 120 and provide a passage for the fluid to flow through the first plurality of loops 120. In one embodiment, the plurality of outlet openings 502 of the first plurality of loops 120 may provide a smooth transition of the fluid when directed by the plurality of flow control valves 126. The plurality of outlet openings 502 of the first plurality of loops 122 may be integrated at one side end of the first portion 102 of the main body.

In one embodiment, the tee-fitting 110 may be made from a material selected from a group of materials including plastic, polymer, polyvinylchloride (PVS), high-density polyethylene (HDPE), rubber, stainless steel, and alike. In one embodiment, the anchor fitting 114 may be made from a material selected from a group of materials of stainless steel, alloy steel, brass, and any possible metal alloy to withstand a load of the main body. In an embodiment, the tether line 116 may be connected on an inner inside of the wall-box apparatus 100 via the anchor fitting 114 bolted into the wall-box apparatus 100. It can be noted that the tether line 116 may be attached to the fly loop combo line 118 that goes to the dialysis machine. The fluid then flows down to the connection that connects at the dialysis machine, then flows back to the tee-fitting 110 and into the first plurality of loops 120 flowing outward from the treatment facility wall-box. In another embodiment, the fly loop combo line 118 may create a continuous flow of fluid to the connection at the dialysis machine. It can be noted that the continuous flow of the fluid eliminates dead leg areas of the fluid loop line created when the fluid may rest or sit within the fluid loop lines which makes the conditions for bacterial growth less likely to occur.

Figure 7:
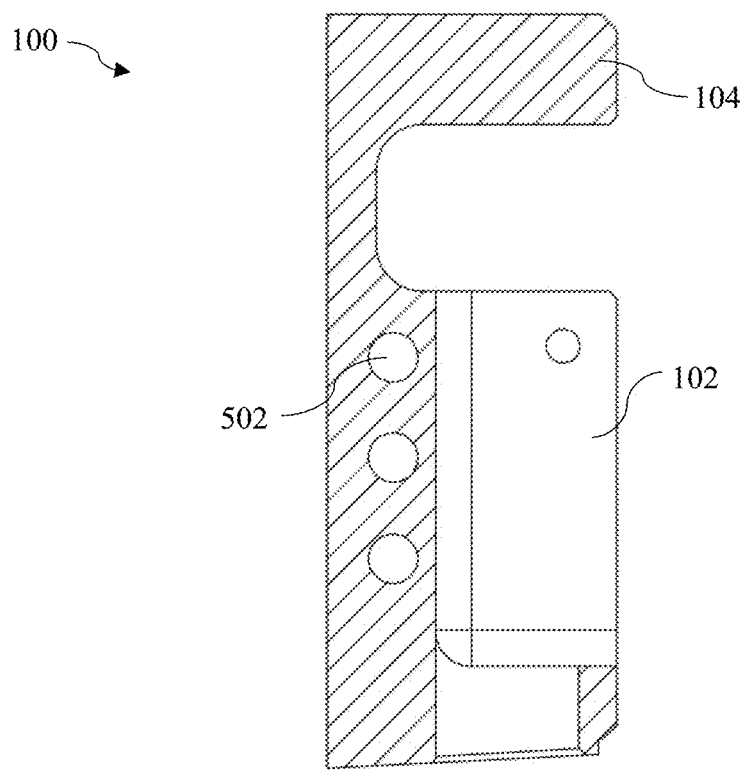
FIG. 7 illustrates a side view of the dialysis treatment facility wall-box apparatus with the plurality of loops, according to an embodiment of the present disclosure.

FIG. 7 illustrates a side view of the dialysis treatment facility wall-box apparatus 100, according to an embodiment. The wall-box apparatus 100 comprises the first portion 102 of the main body, the second portion 104 of the main body, and the plurality of outlet openings 502 of the first plurality of loops 120. The plurality of outlet openings 502 of the first plurality of loops 120 may receive fluid, such as the RO water passing through the first plurality of loops 120. In one embodiment, the first portion 102 may comprise a plurality of outlet openings integrated at one side of the first portion 102 of the main body, for the first plurality of loops 120. In another embodiment, the first portion 102 may comprise at least three outlet openings for at least three loops. It can be noted that the flow of fluid into the first plurality of loops 120 may be directed by the plurality of flow control valves 126. In one exemplary embodiment, at least three flow control valves are integrated for the at least three loops connected via at least three outlet openings.

FIG. 8 illustrates a front view of the dialysis treatment facility wall-box apparatus 100. The wall-box apparatus 100 may comprise a plurality of loop lines 802 and a plurality of plumbing lines 804 integrated within the first portion 102 of the main body. The plurality of loop lines 802 may interact with the plurality of plumbing lines 804 at the plurality of flow control valves 126. It can be noted that each of the plurality of plumbing lines 804 may be mechanically coupled with each of the plurality of loop lines 802. Further, the plurality of plumbing lines 804 may be aligned towards the second outlet opening 304 of the plurality of valves 124 towards the bottom side of the first portion 102. In one embodiment, the plurality of loop lines 802 may be arranged longitudinally along a length of the wall-box apparatus 100, and the plurality of plumbing lines 804 may be arranged transversely along with a height of the wall-box apparatus 100.

In one embodiment, the plurality of plumbing lines 804 may be extended to an interior of the building structure and up to the dialysis machine. It can be noted that the plurality of plumbing lines 804 may be directly coupled with the fluid flow conduits and extending towards the interior of the building structure. In one embodiment, the fluid flow conduits may be coupled with the connecting ports for receiving the plurality of loop lines 802, the plurality of plumbing lines 804, and/or plumbing fittings, such as valves. In one embodiment, the fluid flow conduits may form connecting channels inside the wall-box apparatus 100 for allowing fluid flow communication between the plurality of loop lines 802, the plurality of plumbing lines 804, the plurality of valves 124, and plumbing fittings. In an embodiment, the plurality of loop lines 802 and the plurality of plumbing lines 804 may be made from a material selected from a group of materials including stainless steel, alloy steel, rubber, and plastic.

In one alternate embodiment, the wall-box apparatus 100 may comprise a plurality of fluid flow conduits configured to accommodate fluid flow control and communication between a plurality of fluid sources in the dialysis treatment facility. The wall-box apparatus 100 may comprise a plurality of connecting ports configured at the terminus of the plurality of conduits for connecting to the dialysis machine. In one embodiment, each fluid flow conduit of the plurality of fluid flow conduits may terminate without a corresponding connecting port on different surfaces, with each different surface representing a left side, a right side, a front side, and a bottom side of the wall-box apparatus 100, respectively. For the sake of clarity, any two different surfaces are on opposite faces of the wall-box apparatus 100. In one embodiment, each fluid flow conduit and each connecting port may be fashioned as straight diameter holes, conical holes, chamfered holes, or any suitable shape, without departing from the scope of the disclosure. In another embodiment, each fluid flow conduit and each connecting port may be configured as smooth, threaded, notched, or other construction suitable for connecting to loops, plumbing lines, valves, or fittings, respectively. In one embodiment, the plurality of fluid flow conduits may be straight, curved, or otherwise configured, and may be smooth, threaded, or otherwise finished for connecting to other internal fluid flow conduits. It is contemplated that the wall-box apparatus 100 may be integrated with one or more fluid-flow conduits configured with or without connecting port terminating on the different surfaces. It can be noted that the plurality of fluid flow conduits, extending from connecting ports, are fluid transport holes' machine drilled or otherwise formed, such as separately molded components of the wall-box apparatus 100, electrical discharge machining within the wall-box apparatus 100. In one exemplary embodiment, the wall-box apparatus 100 may be sized such that, fluid lines have minimum wall thickness T to withhold internal pressure of fluids being transported there-through.

In one embodiment, the connecting ports may be counter-bored or countersunk, straight, curved, or may be otherwise configured at different surfaces, and may be smooth, threaded, or otherwise finished for connecting to the plurality of plumbing lines 804, the plurality of loop lines 802, pipes, fittings, etc., as commonly known in the plumbing art. Referring to FIG. 1, the plurality of flow control valves 126 may act as plumbing fittings for regulating the flow of dialysis treatment fluids between the first plurality of loops 120 and a kidney dialysis machine (not shown) via plumbing lines. In one embodiment, the dialysis treatment fluids may include, but not limited to, RO water, distilled water, acid concentrates, and bicarbonate concentrates dialysate.

In one embodiment, the wall-box apparatus 100 may eliminate an assembly of the building structure's electrical connections, data lines, and the like within, or within proximity to, the wall-box apparatus 100. It can be noted that utilities such as, electrical connections, data lines, and alike may be located elsewhere on a wall, thereby removing the fluid lines of the building and the wall-box apparatus 100, as traditionally constructed, from proximity to them. In another embodiment, the plumbing lines, such as the first plurality of loops 120 connected to the wall-box apparatus 100, generally run along a wall and may be concealed by a bumper guard rail of sufficient width to conceal loops.

Figure 9:
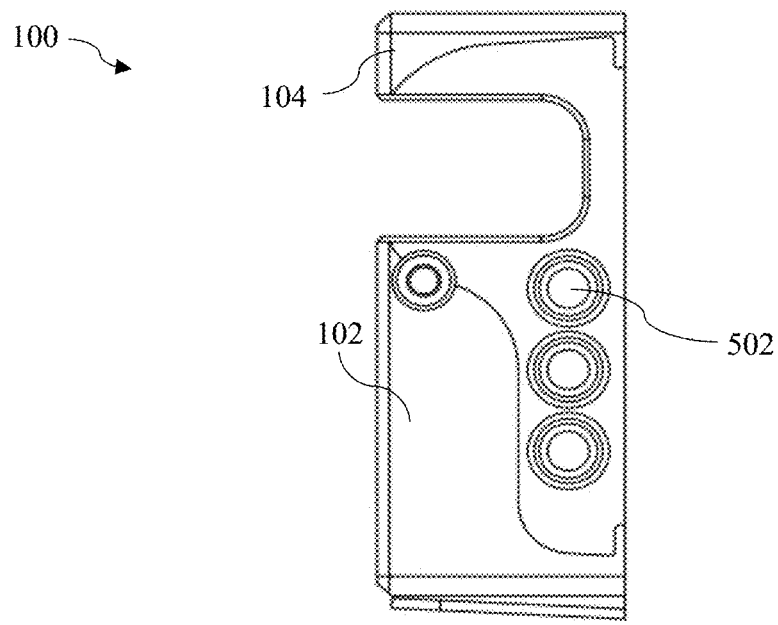
FIG. 9 illustrates another side view of the dialysis treatment facility wall-box apparatus, according to another embodiment of the present disclosure.

FIG. 9 illustrates another side view of the dialysis treatment facility wall-box apparatus 100, according to another embodiment. The wall-box apparatus 100 may comprise the first portion 102 of the main body, the second portion 104 of the main body, and the plurality of outlet openings 502 of the first plurality of loops 120. The plurality of outlet openings 502 of the first plurality of loops 120 may receive fluids such as RO water, passing through the first plurality of loops 120. It can be noted that the plurality of outlet openings 502 of the first plurality of loops 120 may be positioned below the first portion 102 of the main body and on surface of the second portion 104 of the main body.

Figure 10:
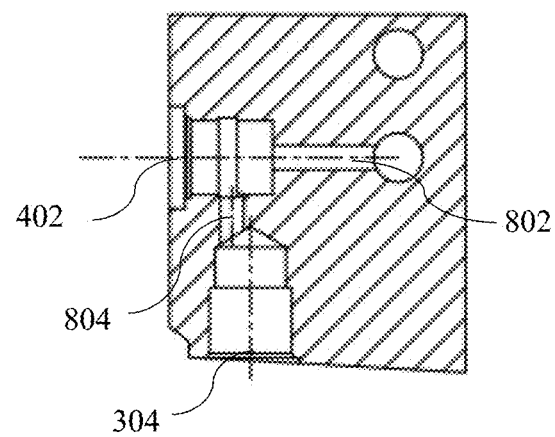
FIG. 10 illustrates a sectional view of the dialysis treatment facility wall-box apparatus, according to another embodiment of the present disclosure.

FIG. 10 illustrates a sectional view of the dialysis treatment facility wall-box apparatus 100, according to an embodiment. The wall-box apparatus 100 may comprise the second outlet opening 304 of the plurality of valves 124, the plurality of outlet openings 402 of the second plurality of loops 122, the plurality of loop lines 802, and the plurality of plumbing lines 804. The plurality of plumbing lines 804 may be mechanically coupled with the plurality of valves 124 and the plurality of outlet openings 402 of the second plurality of loops 122. In one embodiment, the plurality of loop lines 802 may be mounted on the plurality of plumbing lines 804 at a direction perpendicular to the plurality of outlet openings 402 of the second plurality of loops 122. In an embodiment, the plurality of plumbing lines 804, such as loops, connected to wall-box apparatus 100, generally run along a wall, and may be concealed by a bumper guard rail of sufficient width to conceal the loops.

Figure 11:
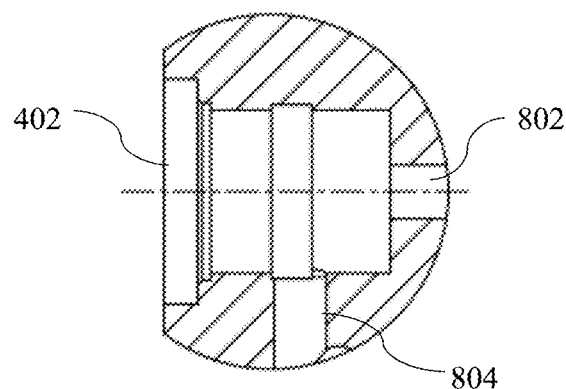
FIG. 11 illustrates another sectional view of the dialysis treatment facility wall-box apparatus, according to another embodiment of the present disclosure.

FIG. 11 illustrates another sectional view of the dialysis treatment facility wall-box apparatus 100, according to an embodiment. The wall-box apparatus 100 may comprise the plurality of outlet openings 402 of the second plurality of loops 122, the plurality of loop lines 802, and the plurality of plumbing lines 804. The plurality of loop lines 802 may be mounted on the plurality of plumbing lines 804 at a direction perpendicular to the plurality of outlet openings 402 of the second plurality of loops 122. In one alternate embodiment, the wall-box apparatus 100 may comprise a clip to snap in fluid lines up to one fluid line and three bicarb and acid lines. In one embodiment, the clip may provide an easy and organized way to snap in the fluid lines up to a total of four fluid lines. In another embodiment, the clip may serve as a fastener for a P-shaped bumper railing for snap-on functions.

Figure 12:
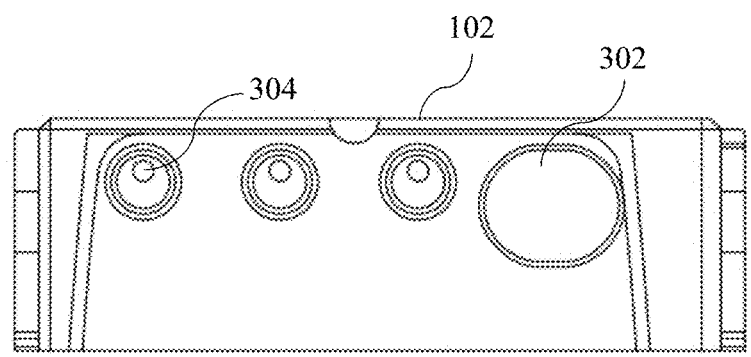
FIG. 12 illustrates a bottom view of the dialysis treatment facility wall-box apparatus, according to another embodiment of the present disclosure.

FIG. 12 illustrates a bottom view of the dialysis treatment facility wall-box apparatus 100, according to another embodiment. The wall-box apparatus 100 may comprise the first portion 102 of the main body, the first outlet opening 302 of the fly loop combo line 118, and the second outlet opening 304 of the plurality of valves 124. The first outlet opening 302 of the fly loop combo line 118, and the second outlet opening 304 of the plurality of valves 124 may be integrated towards the bottom side of the first portion 102 of the main body. In one embodiment, the wall-box apparatus 100 may comprise at least three second outlet openings for at least three valves. It can be noted that the second outlet opening 304 may vary according to the valves required for each dialysis machine. In one embodiment, the wall-box apparatus 100 may be constructed to have at least three valves and at least three outlet openings.

Figure 13:
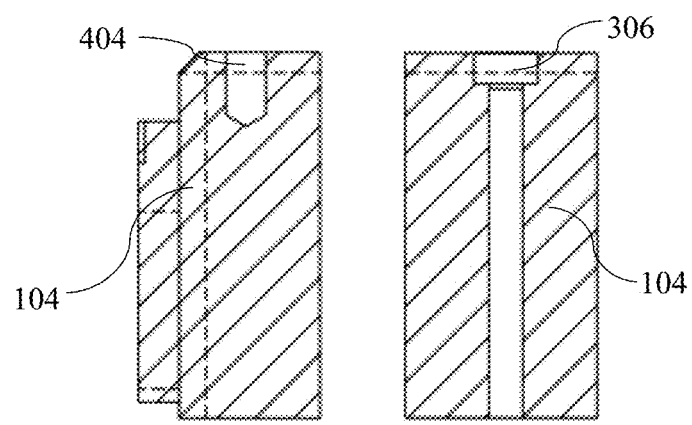
FIG. 13 illustrates a top view of a top section of the dialysis treatment facility wall-box apparatus, according to another embodiment of the present disclosure.

FIG. 13 illustrates a top view of a top section of the dialysis treatment facility wall-box apparatus 100, according to another embodiment. The wall-box apparatus 100 may comprise the second portion 104 of the main body, the first plurality of holes 306, and the second plurality of holes 404. The first plurality of holes 306 and the second plurality of holes 404 may be integrated to the second portion 104 of the main body. In one embodiment, the first plurality of holes 306 may be thorough holes integrated onto the second portion 104 of the main body. The second plurality of holes 404 may be small threaded holes to receive the second plurality of screws 210. In one embodiment, the wall-box housing 202 may be coupled to the main body using the second plurality of holes 404 and the second plurality of screws 210. Further, the first plurality of holes 306 may be provided to mount the wall-box apparatus 100 onto a wall or any vertical surface of the building structure.

Figure 14:
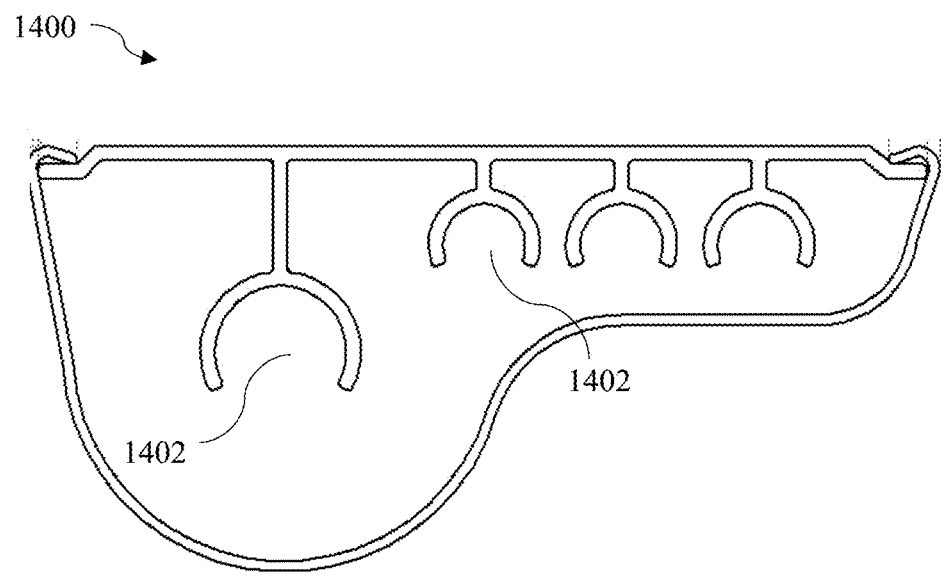
FIG. 14 illustrates a bumper clip configured to serve as a fastening means for a P-shaped bumper railing, according to another embodiment of the present disclosure

FIG. 14 illustrates a bumper clip 1400 configured to serve as a fastening means for a P-shaped bumper railing, according to another embodiment. The bumper clip 1400 may be configured to provide an organized manner for snapping fluid lines and to serve as a fastening means for a P-shaped bumper railing to snap onto the bumper clip 1400. Further, the bumper clip 1400 may comprise a plurality of provisions 1402 to snap or hold the fluid lines coming out of the wall-box apparatus 100. In one embodiment, the bumper clip 1400 may be positioned towards the bottom side of the first portion 102 of the wall-box apparatus 100. In one exemplary embodiment, the bumper clip 1400 may snap the fly loop combo line 118 and supply connections coupled to the plurality of valves 124. It can be noted that the bumper clip 1400 may be provided to eliminate a requirement of shelves and cabinets to increase space for the dialysis treatment facility and thereby increasing available space.

Figure 15:
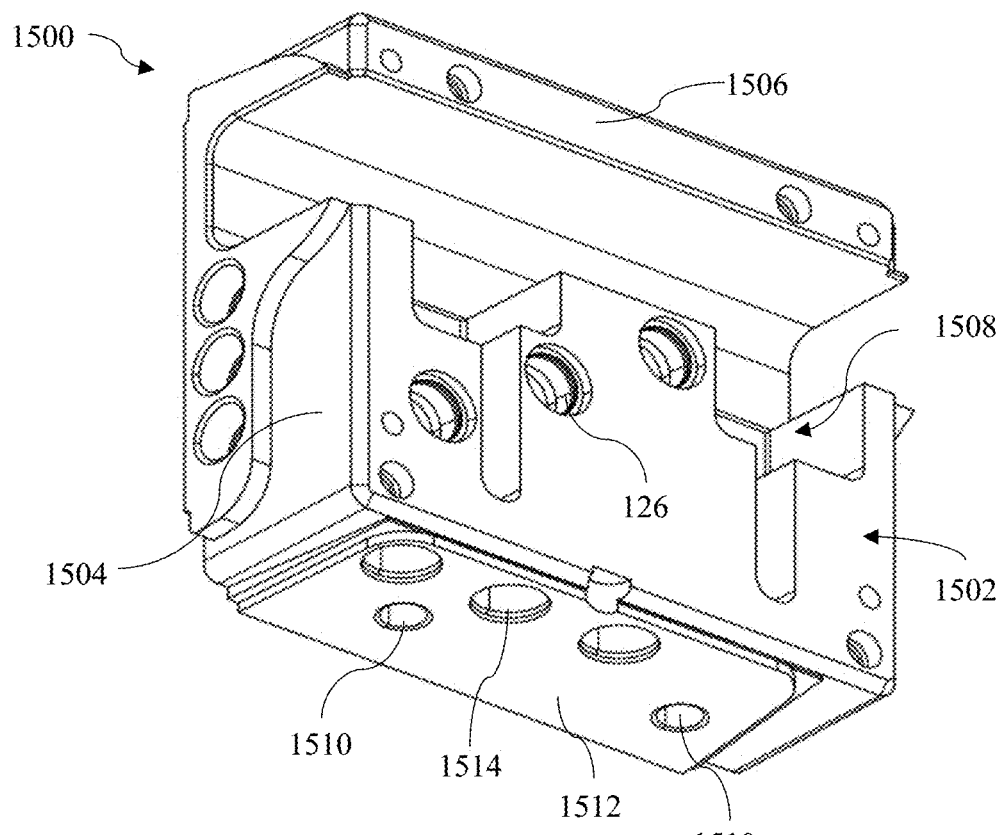
FIG. 15 illustrates a perspective view of a multi-outlet dialysis treatment facility wall-box apparatus, according to another embodiment of the present disclosure.
Figure 16:
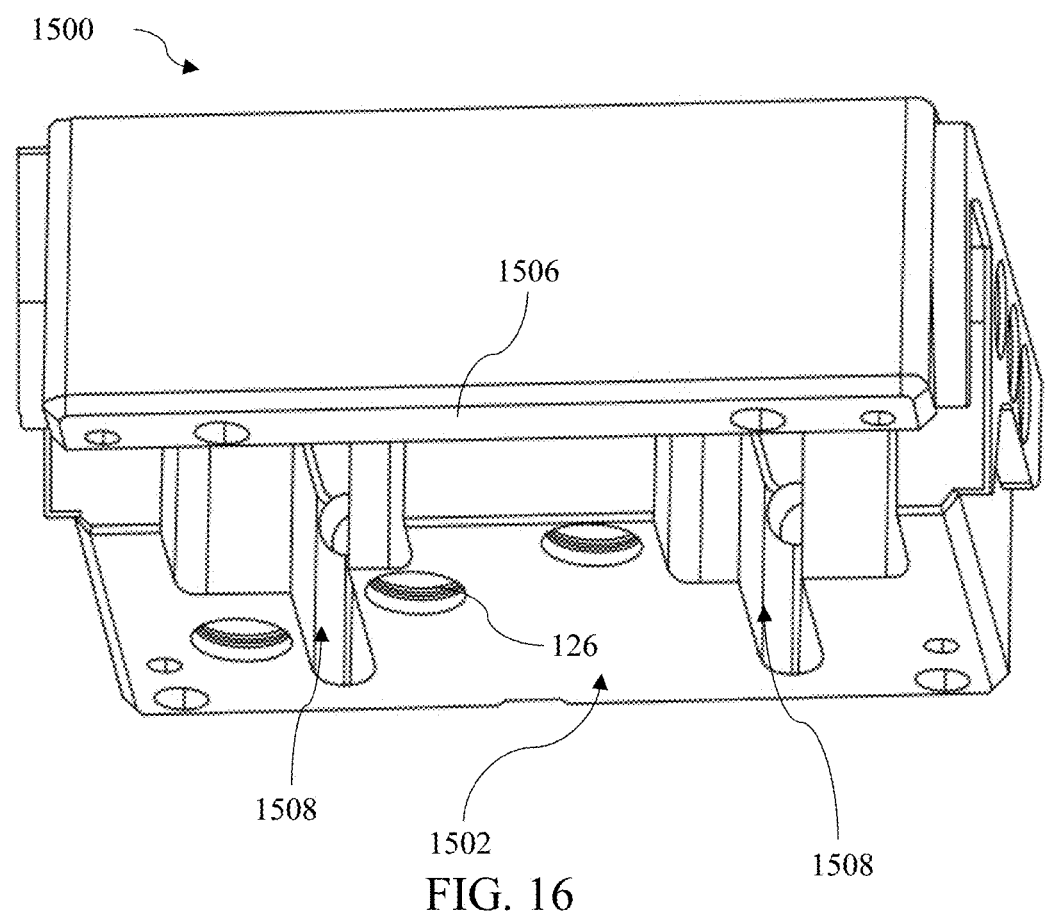
FIG. 16 illustrates a top perspective view of the multi-outlet dialysis treatment facility wall-box apparatus, according to another embodiment of the present disclosure.
Figure 17:
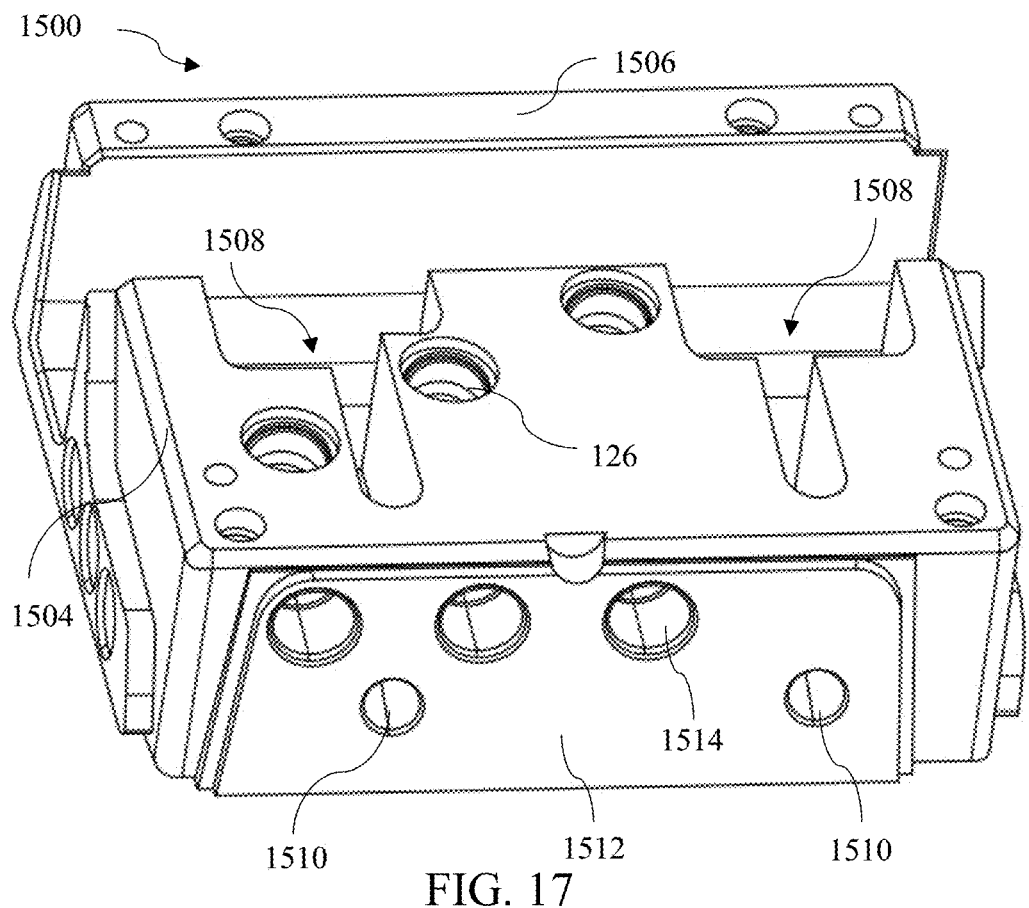
FIG. 17 illustrates a bottom perspective view of the multi-outlet dialysis treatment facility wall-box apparatus, according to another embodiment of the present disclosure

In one alternate embodiment, referring to FIGS. 15-17 which illustrate perspective views of a multi-outlet dialysis treatment facility wall-box apparatus 1500. Hereinafter, the multi-outlet dialysis treatment facility wall-box apparatus 1500 may be referred as an another wall-box apparatus 1500. The another wall-box apparatus 1500 may comprise a front surface 1502 and a rear surface (not shown). The front surface 1502 of the wall-box apparatus may comprise a first part 1504 and a second part 1506. It can be noted that the first part 1504 and the second part 1506 may be spaced from each other. Further, the first part 1504 may comprise a plurality of stepped provisions 1508 integrated longitudinally on the front surface 1502 of the another wall-box apparatus 1500. In one embodiment, the plurality of stepped provisions 1508 may be provided for receiving a plurality of tee-fittings (not shown). It can be noted that the plurality of tee-fittings may be positioned in a space between the first part 1504 and the second part 1506 of the front surface 1502 of the another wall-box apparatus 1500. It can also be noted that the plurality of stepped provisions 1508 may be referred as integrated tee-fittings.

Further, the front part 1504 of the front surface 1502 of the another wall-box apparatus 1500 may comprise the plurality of flow control valves 126 positioned transversely into the front surface 1502 of the wall-box apparatus 1500. It can be noted that the plurality of flow control valves 126 may protrude normal to the front surface 1502 and the rear surface of the another wall-box apparatus 1500. In one embodiment, each of the plurality of flow control valves 126 may perform functions in a similar fashion as explained in FIGS. 1-9.

Further, the another wall-box apparatus 1500 may comprise a first plurality of outlet openings 1510 positioned towards a bottom surface 1512 of the first part 1504 of the another wall-box apparatus 1500. The first plurality of outlet openings 1510 may be integrated below the plurality of stepped provisions 1508 to receive fluid from the plurality of tee-fittings. It can be noted that the first plurality of outlet openings 1510 may be coupled to a plurality of fly loop combo lines (not shown) to provide a passage for continuous flow of the fluid to the connection at multiple dialysis machines. Further, the another wall-box apparatus 1500 may comprise a second plurality of outlet openings 1514 positioned towards the bottom surface 1512 of the first part 1504 of the another wall-box apparatus 1500. It can be noted that the plurality of valves 124 may push out the flow of fluid through the second plurality of outlet openings 1514, to regulate the flow of the fluid. In one embodiment, the first part 1504 may comprise at least two stepped provisions to receive at least two tee-fittings which may be further coupled to at least two fly loop combo lines to provide a passage for continuous flow of the fluid to the connection at two dialysis machines.

Figure 18:
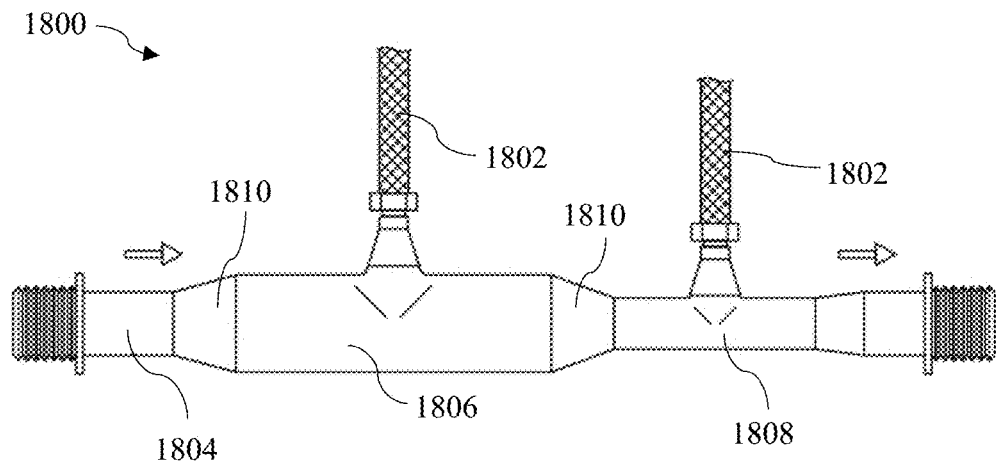
FIG. 18 illustrates an exemplary view of a second tee-fitting of the dialysis treatment facility wall-box apparatus, according to another embodiment of the present disclosure.
Figure 20:
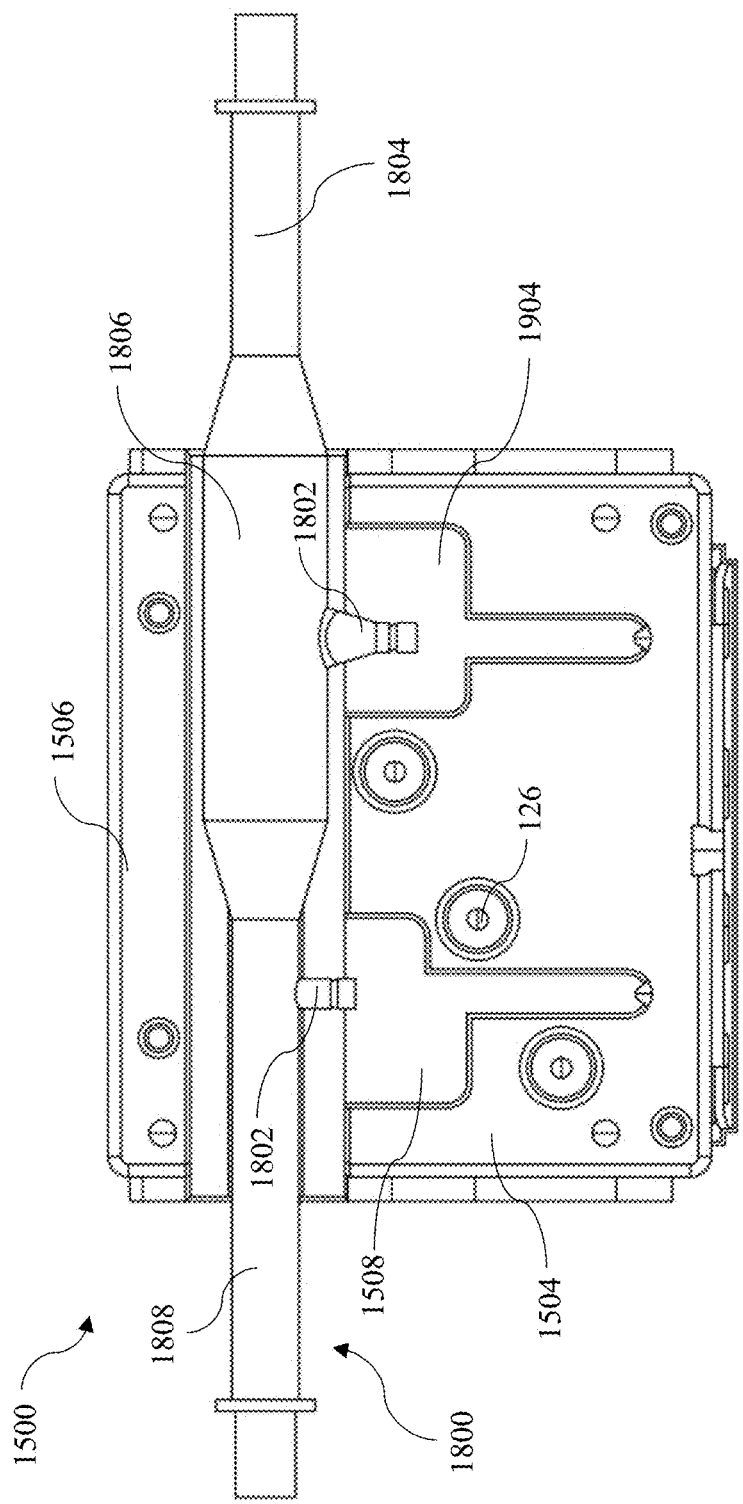
FIGS. 20-21 illustrate the multi-outlet dialysis treatment facility wall-box apparatus coupled with the second tee-fitting, according to an exemplary embodiment of the present disclosure.
Figure 21:
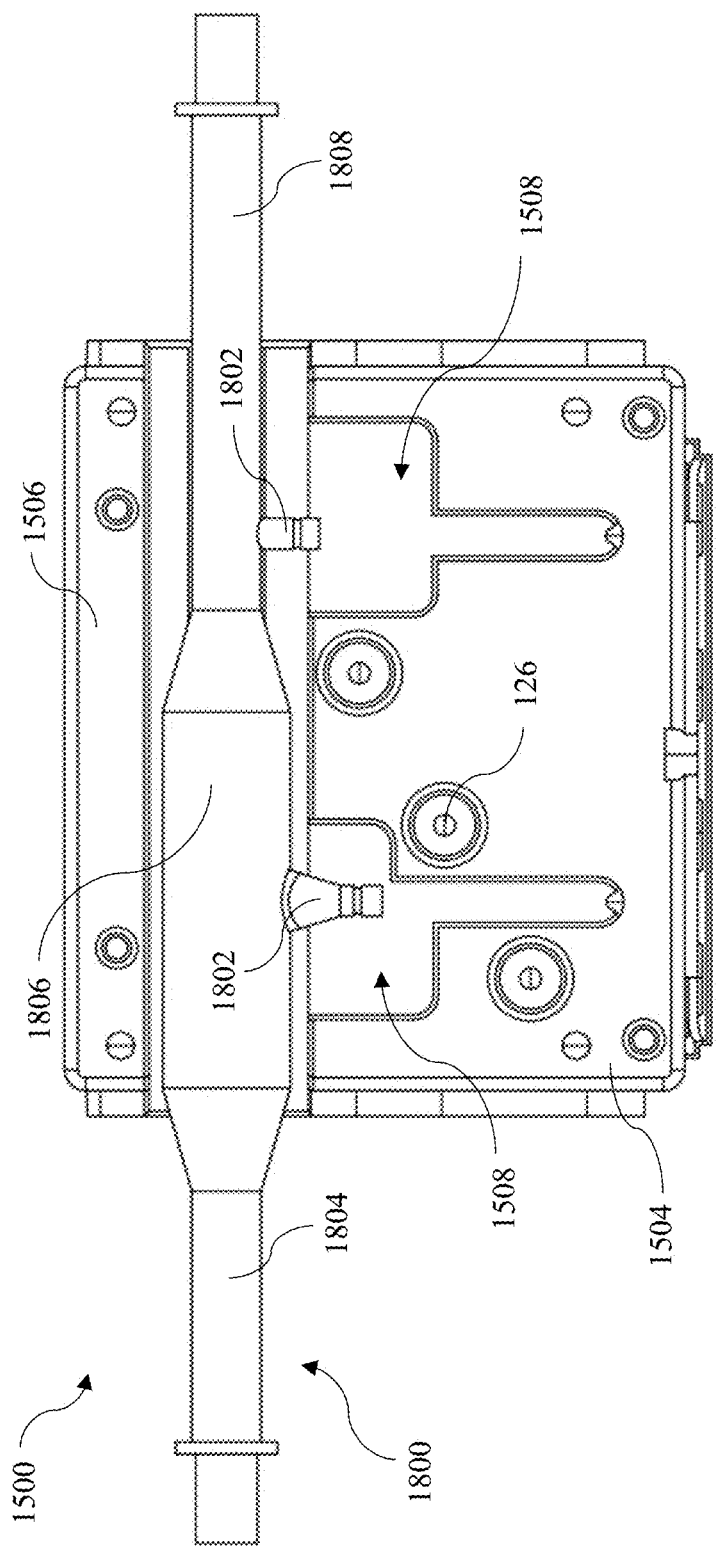

FIG. 18 illustrates an exemplary view of an another tee-fitting 1800 of the dialysis treatment facility wall-box apparatus, according to another embodiment. FIG. 18 is described in conjunction with FIGS. 20-21. The another tee-fitting 1800 may be integrated with the plurality of fly loop lines 112. Further, the another tee-fitting 1800 may be positioned between the first part 1504 and the second part 1506 of the another wall-box apparatus 1500. The another tee-fitting 1800 may comprise a plurality of connection lines 1802 integrated at multiple positions along a length of the another tee-fitting 1800, as shown in FIGS. 20-21. The plurality of connection lines 1802 may extend transversely to the length of the another tee-fitting 1800. It can be noted that the another tee-fitting 1800 may be a pipe with multiple cross-sections, with fluid flowing from one end to other end. In one embodiment, the another tee-fitting 1800 may be referred as a differential pressure valves or a secondary loop, positioned between the first part 1504 and the second part 1506 of the another wall-box apparatus 1500.

Further, the another tee-fitting 1800 may comprise a first cross-sectional part 1804, a second cross-sectional part 1806, and a third cross-sectional part 1808. In one embodiment, the first cross-sectional part 1804 may have a smaller cross-section than the second cross-sectional part 1806, to decrease pressure and speed of the fluid flowing from the first cross-sectional part 1804 towards the second cross-sectional part 1806. Similarly, the third cross-sectional part 1808 may have a smaller cross-section than the second cross-sectional part 1806 and the first cross-sectional part 1804, to increase pressure and speed of fluid flowing towards the third cross-sectional part 1808. It can be noted that the another tee-fitting 1800 may induce a throttling effect at connecting parts 1810 connecting the first cross-sectional part 1804 and the second cross-sectional part 1806, the second cross-sectional part 1806 and the third cross-sectional part 1808. Further, the another tee-fitting 1800 may be coupled to the fluid inlet 106 and the fluid outlet 108, as described earlier in FIGS. 1-9. In one embodiment, the another tee-fitting 1800 may be provided for supplying fluid out of the another wall-box apparatus 1500 to the multiple dialysis machines and back to the another tee-fitting 1800 via the fly loop combo line 118. It can be noted that the plurality of connections lines 1802 of the another tee-fitting 1800 may be coupled to a plurality of fly loop combo lines (not shown) in a similar manner as the fly loop combo line 118 of FIGS. 1-2.

Figure 19:
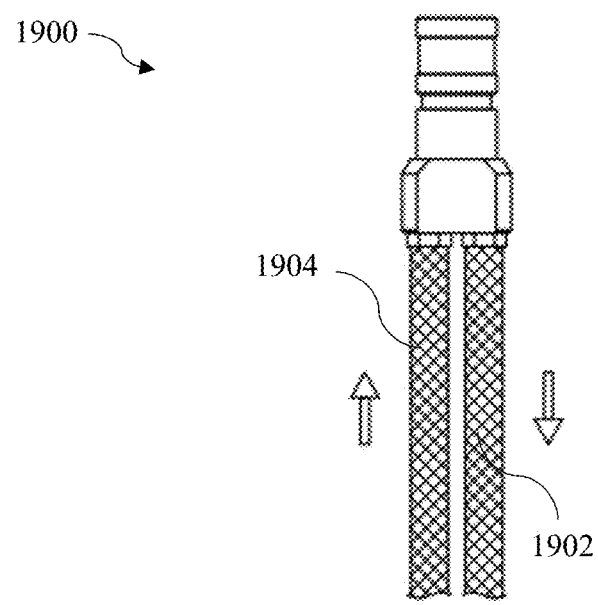
FIG. 19 illustrates a front view of a connection line of the second tee-fitting coupled with the dialysis treatment facility wall-box apparatus, according to another embodiment of the present disclosure.

FIG. 19 illustrates a front view of a connection line 1900 of the another tee-fitting 1800 integrated within the another wall-box apparatus 1500, according to another embodiment. The connection line 1900 may comprise a first fly loop line 1902 configured to supply fluid downwards to the multiple dialysis machines. Further, the connection line 1900 may a second fly loop line 1904 configured to supply fluid towards the another wall-box apparatus 1500 from the multiple dialysis machines. In one embodiment, the connection line 1900 may be referred as a secondary ring. The connection line 1900 may be connected to the hemodialysis machine. In another embodiment, the connection line 1900 may be referred as a distribution bulb, to eliminate dead space between the main distribution line and the dialysis machine. In one exemplary embodiment, the connection line 1900 may be made from 316L stainless steel female connector. In another exemplary embodiment, the connection line 1900 may be 3000 mm to 7000 mm in length, depending upon the size of the hemodialysis machine and the wall-box apparatus 100.

FIGS. 20-21 illustrate the multi-outlet dialysis treatment facility wall-box apparatus coupled with the second tee-fitting, according to an exemplary embodiment of the present disclosure. In one embodiment, the another wall-box apparatus 1500 may be configured to receive the another tee-fitting 1800 between the first part 1504 and the second part 1506 of the another wall-box apparatus 1500. It can be noted that the another tee-fitting 1800 may be provided with at least two connections lines of the plurality of connection lines 1802. It can also be noted that the another tee-fitting 1800 may allow elimination of using multiple wall-box apparatuses to account for fly loops or pipes coming from multiple positions and locations in the dialysis treatment facility. The another wall-box apparatus 1500 provides Bernoulli T-box to minimize amount of space/real estate required for dialysis treatment facilities. In one embodiment, the fluid flowing through the another tee-fitting 1800 and the plurality of connection lines 1802 employ a Bernoulli effect. For example, a pressure decrease is associated with an increase in fluid speed, and increased pressure is associated with a decrease in fluid speed. Further, the another wall-box apparatus 1500 may be provided with the first plurality of outlet openings 1510 to be coupled with the fly loop combo lines to regulate flow of fluid with increase in pressure when flowing upwards to the another tee-fitting 1800 and with decrease in pressure when flowing towards the dialysis treatment machines.

Figure 22:
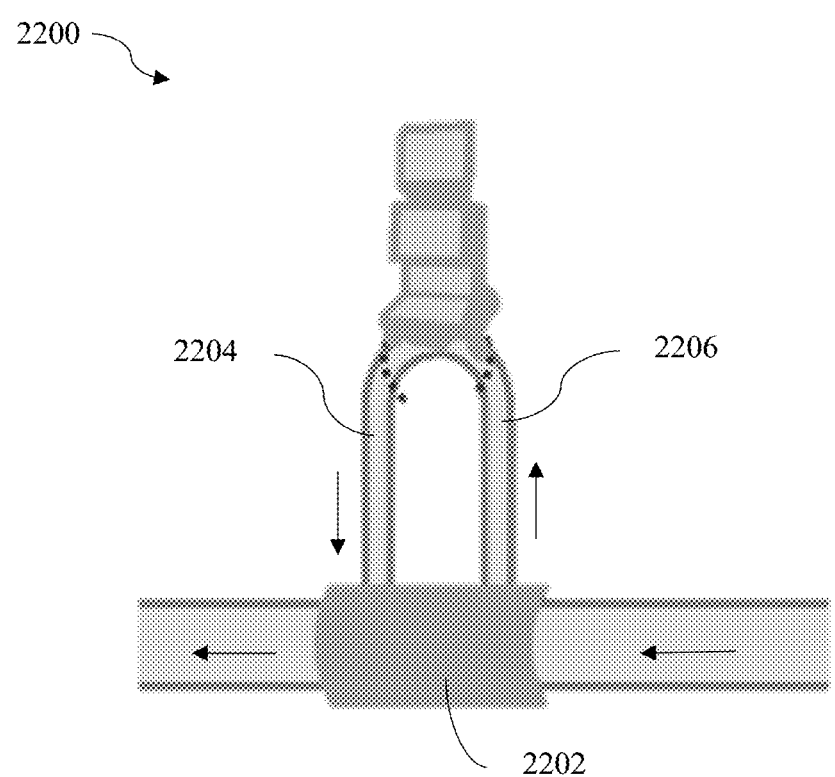
FIG. 22 illustrates a dead space valve, according to another embodiment of the present disclosure.

FIG. 22 illustrates a dead space valve 2200, according to another embodiment of the present disclosure. FIG. 22 is described in conjunction with FIGS. 1-21. The dead space valve 2200 may comprise a primary ring piping 2202, a secondary ring piping 2204, a coupling with double adapter 2206. The secondary ring piping 2204 may be transversely coupled to the primary ring piping 2202 to direct flow into the primary ring piping 2202. It can be noted that the secondary piping ring 2204 and the coupling with double adapter 2206 may form a ring shaped structure, for supplying and receiving the fluid to and from the dialysis machine. It can be noted that the flow may be directed from the primary ring piping 2202 into the coupling with double adapter 2206 into the dialysis machine and the secondary ring piping 2204 may receive the output fluid from the dialysis machine into the primary ring piping 2202, and back into the wall-box apparatus 100.

In one embodiment, the ring shaped structure of the primary ring piping 2202 and the secondary ring piping 2204 may prevent formation of a biofilm inside the valve 2200. It can be noted that the biofilm may include, formation of microorganisms, exotoxins and endotoxins. The 2200 prevents the formation of infections during continuous supply of fluid, flowing in and out of the dialysis machine and the wall-box apparatus 100. In one embodiment, the valve 2200 may be referred to as a Bernoulli valve. It can be noted that the valve 2200 may enable a constant flow in hose connection to the dialysis machine.

FIGS. 23A-23D illustrate a wall-box apparatus 100 mounted inside the wall of the dialysis facility room, according to another embodiment of the present disclosure. FIGS. 23A-23D is described in conjunction with FIGS. 1-9 and FIGS. 15-21. The wall-box apparatus 100 may be mounted inside the wall of the dialysis facility room to eliminate the need for dead space piping and enhance ergonomic and hygiene aspects. The wall-box apparatus 100 may comprise a permeate water outlet 2302, a hemodialysis machine drain connection 2304, at least three acid concentrate connections 2306, a backing plate 2308 and a molded concrete block 2310 for the plurality of flow control valves 126, as shown in FIG. 1. In one embodiment, the wall-box apparatus 100 may be referred as a media providing center for supplying fluid medium to the dialysis machine.

Further, the permeate water outlet 2302 may be integrated on the wall-box housing as shown in FIG. 2 and hemodialysis machine drain connection 2304 may be provided for discharging fluid out of the wall-box apparatus 100 after received from the dialysis machine. It can be noted that the at least three acid concentrate connections 2306 may be integrated on the wall-box housing. Further, the wall-box apparatus may be provided with the backing plate 2308 to mount the wall-box apparatus 100 onto the wall of the dialysis facility room using screws. Further, the wall-box apparatus 100 may be provided with the molded concrete block 2310 for integration of the plurality of flow control valves 126, to maintain even distribution of flow and pressure according to the Bernoulli's effect. The wall-box apparatus 100 may be compact to be mounted inside the wall and eliminate the need for arrangement of pipes and fittings, and thereby reducing dead space inside the dialysis facility room.

In one exemplary embodiment, the wall-box apparatus 100 may reduce operating cost for dialysis providers, such as, hospitals, medical care facilities, etc. In another exemplary embodiment, the present invention may produce water with lower levels of toxins and bacteria, thereby reducing additional costs related to prevention of infections in current dialysis machines. In another exemplary embodiment, the wall-box apparatus 100 may be made from a material selected from a group of materials of stainless steel, and alloy steel, to increase durability of the wall-box apparatus 100. Further, the wall-box apparatus 100 may have low operating cost, low water utilization and very low risk profile. The wall-box apparatus 100 may also provide smaller footprints which may reduce space requirements and construction costs for new dialysis treatment facilities. It can be noted that that wall-box apparatus 100 may also have fewer breakdowns, due to redundant reverse osmosis (RO) and pumps, which increase breakdowns of the wall-box apparatus 100.

In one exemplary embodiment, the wall-box apparatus 100 is a dead space free reverse osmosis design. It can be noted that the elimination of dead space is critical to mitigating the development of biofilm and limiting bacteria proliferation. It can also be noted that the wall-box apparatus 100 is a dead space free distribution system with dead space free secondary loops. Further, the wall-box apparatus 100 is a dual stage reverse osmosis unit, which improves water quality and reduces water consumption. Further, the wall-box apparatus 100 provides an impulse backwashing, which improves membrane performance, water quality and reduce overall costs. In one embodiment, the wall-box apparatus 100 is a complete heat disinfection, by allowing a chemical free sterilization and improves water quality. It can also be noted that the wall-box apparatus 100 minimizes risks of patient exposure to harmful chemicals. In one exemplary embodiment, the wall-box apparatus 100 may be made from a stainless steel material to minimize risk of failure and breakdown. Further, the wall-box apparatus 100 may be communicatively coupled with a software interface for central monitoring of the complete dialysis system.

In an alternate exemplary embodiment, the wall-box apparatus 100 may be attached to a building wall using screws, glue, or other attachment means (not shown). In one embodiment, a funnel means, in addition to the wall-box apparatus 100, may be provided to allow flexibility in locating the funnel means for access to a building's waste drain line. In another alternate exemplary embodiment, the wall-box apparatus 100 may be configured to provide concurrent fluid flow communication to the plurality of dialysis machines on opposite sides of the facility wall.

Thus, it is seen, in accordance with the disclosure herein and the accompanying drawings, that at least one embodiment of the dialysis treatment facility wall-box apparatus 100 provides more reliable infection control, by eliminating joints and reducing fluid infection in the wall-box apparatus 100, while also reducing the amount of space required for a wall chase system in a kidney-dialysis treatment facility. Furthermore, the wall-box apparatus 100 has an additional advantage in that it simplifies fluid transport for enhanced reliability by reducing the number of plumbing lines and fittings. In an exemplary embodiment, it is contemplated that wall-box apparatus 100 may be configured as an interface panel (comprising plumbing lines, fittings, valves, etc.) closely and directly mounted to a facility wall that provides connections to building and kidney-dialysis machine plumbing lines.

Those skilled in the art would appreciate that features (e.g., connection ports, fittings, valves, etc.) on all surfaces of the wall-box apparatus 100 are interchangeable with adjoining and/or opposite surfaces without loss of functionality. Relocation of features in such a manner would be done, for example, to accommodate treatment facility available space and configuration constraints.

While the above description contains many specificities, these should not be construed as limitations on the scope, but rather as an exemplification of one embodiment thereof It should be understood that the broadest scope of this invention includes modifications such as diverse shapes, sizes, and materials. Accordingly, the scope of the present invention should be determined, not by the embodiments illustrated, but by the appended claims and their legal equivalents.

While there is shown and described herein certain specific structures embodying various embodiments of the invention, it will be manifest to those skilled in the art that various modifications and rearrangements of the parts may be made without departing from the spirit and scope of the underlying inventive concept and that the same is not limited to the particular forms herein shown and described except insofar as indicated by the scope of the appended claims.

What is claimed is:

1. A dialysis treatment facility wall-box apparatus comprising:
    a main body having a first portion and a second portion spaced apart from the first portion, enclosed in a wall-box housing;
    a tether line connected to the first portion of the main body using an anchor fitting, wherein the anchor fitting is integrated to the first portion of the main body;
    a tee-fitting positioned in a space between the first portion and the second portion of the main body, wherein the tee-fitting is coupled to the anchor fitting through a plurality of fly loop lines protruding towards the first portion of the main body;
    a first plurality of loops positioned at a first end of the main body and a second plurality of loops positioned at a second end of the main body, wherein the first plurality of loops and the second plurality of loops extend normally outwards of the main body; and
    a fly loop combo line coupled to the first portion of the wall-box housing at a first end of the fly loop combo line and connected to a dialysis machine at a second end of the fly loop combo line, wherein the fly loop combo line creates a continuous flow of a fluid downwards to the dialysis machine and then flows back to the tee-fitting and into the first plurality of loops.

2. The dialysis treatment facility wall-box apparatus of claim 1, further comprising:
    a fluid inlet attached at a first end of the tee-fitting; and
    a fluid outlet attached at a second end of the tee-fitting, wherein the fluid inlet and the fluid outlet are coupled to the tee-fitting horizontally within the space between the first portion and the second portion of the main body.

3. The dialysis treatment facility wall-box apparatus of claim 1, further comprising:
    a plurality of valves coupled to the first portion of the main body, wherein each of the plurality of valves is detachable from the wall-box housing; and
    a plurality of flow control valves integrated over a surface of the first portion and protruded normal to the surface of the first portion, wherein each of the plurality of flow control valves is configured to facilitate a movement of fluid towards each of the plurality of valves.

4. The dialysis treatment facility wall-box apparatus of claim 1, wherein the first plurality of loops and the second plurality of loops are tightened to the first portion of the main body using a first plurality of screws.

5. The dialysis treatment facility wall-box apparatus of claim 1, wherein the wall-box housing is coupled to the main body using a second plurality of screws and the wall-box housing encloses, the main body coupled with the first plurality of loops, the second plurality of loops, the plurality of flow control valves, the tee-fitting, the anchor fitting, and the tether line.

6. The dialysis treatment facility wall-box apparatus of claim 3, wherein the plurality of flow control valves is coupled with a plurality of valve regulators to regulate a flow of the fluid towards the plurality of valves.

7. The dialysis treatment facility wall-box apparatus of claim 1, further comprising:
    a plurality of fluid flow conduits configured to accommodate fluid flow control and communication between a plurality of fluid sources in the dialysis treatment facility wall-box apparatus; and
    a plurality of connecting ports configured to receive the plurality of loop lines and a plurality of plumbing lines.

8. The dialysis treatment facility wall-box apparatus of claim 1, wherein the dialysis treatment facility wall-box apparatus is configured to reduce the number of joints in plumbing systems.

9. The dialysis treatment facility wall-box apparatus of claim 1, wherein the dialysis treatment facility wall-box apparatus is configured to increase available space in a building.

10. The dialysis treatment facility wall-box apparatus of claim 1, wherein the dialysis treatment facility wall-box apparatus eliminates a requirement of shelves and cabinets to increase space for the dialysis treatment facility.

11. The dialysis treatment facility wall-box apparatus of claim 1, further comprises a bumper clip to provide an organized manner for snapping fluid lines and to serve as a fastening means for a P-shaped bumper railing to snap onto the bumper clip.

12. The dialysis treatment facility wall-box apparatus of claim 11, wherein the fluid lines include at least RO fluid line, one bicarb line and two acid lines.

13. A method of managing fluid flow through a dialysis treatment facility wall-box apparatus, the method comprising:
providing a main body of a wall-box housing with a first portion and a second portion spaced apart from the first portion and enclosed in a wall-box housing;
providing a tether line connected to the first portion of the main body of the wall-box housing via an anchor fitting integrated to the first portion of the main body;
providing a plurality of fly loop lines protruding towards the first portion of the main body of the wall-box housing;
connecting a tee-fitting in a space between the first portion and the second portion of the main body, wherein the tee-fitting is coupled to the anchor fitting through a plurality of fly loop lines protruding towards the first portion of the main body;
positioning a first plurality of loops at a first end of the main body and a second plurality of loops at a second end of the main body, wherein the first plurality of loops and the second plurality of loops extended normally outwards of the wall-box housing; and
connecting a fly loop combo line, coupled to the first portion of the wall-box housing, at a first end of the fly loop combo line, to a dialysis machine, at a second end of the fly loop combo line, for creating a continuous flow of fluid downwards to the dialysis machine, then flows back to the tee-fitting and into the first plurality of loops.

14. The method of claim 13, wherein the first plurality of loops and the second plurality of loops are tightened to the first portion of the main body using a first plurality of screws.

15. The method of claim 13, wherein the wall-box housing is coupled to the main body using a second plurality of screws and the wall-box housing encloses the main body coupled with the first plurality of loops, the second plurality of loops, a plurality of flow control valves, the tee-fitting, the anchor fitting, and the tether line.

16. The method of claim 13, further comprising a plurality of fluid flow conduits configured to accommodate fluid flow control and communication between a plurality of fluid sources in a dialysis treatment facility.

17. The method of claim 13, further comprising:
a fluid inlet attached at a first end of the tee-fitting; and
a fluid outlet attached at a second end of the tee-fitting, wherein the fluid inlet and the fluid outlet are coupled to the tee-fitting horizontally within the space between the first portion and the second portion of the main body.

18. The method of claim 13, further comprising:
a plurality of valves coupled to the first portion of the main body, wherein each of the plurality of valves is detachable from the main body; and
a plurality of flow control valves integrated over a surface of the first portion and protruding normal to the surface of the first portion, wherein each of the plurality of flow control valves is configured to facilitate a movement of fluid towards each of the plurality of valves.

19. The method of claim 13, further comprises a bumper clip to provide an organized manner for snapping fluid lines and to serve as a fastening means for a P-shaped bumper railing to snap onto the bumper clip.

20. The method of claim 19, wherein the fluid lines include one RO fluid line and one bicarb line and two acid lines.

* * * * *